(12) United States Patent
Platzek et al.

(10) Patent No.: US 12,054,481 B2
(45) Date of Patent: Aug. 6, 2024

(54) METHOD FOR THE PREPARATION OF (4S)-4-(4-CYANO-2-METHOXYPHENYL)-5-ETHOXY-2,8-DIMETHYL-1,4-DIHYDRO-1-6-NAPHTHYRIDINE-3-CARBOX-AMIDE BY RACEMATE SEPARATION BY MEANS OF DIASTEREOMERIC TARTARIC ACID ESTERS

(71) Applicants: Bayer Aktiengesellschaft, Leverkusen (DE); Bayer Pharma Aktiengesellschaft, Berlin (DE)

(72) Inventors: Johannes Platzek, Berlin (DE); Kai Lovis, Düsseldorf (DE); Winfried Joentgen, Cologne (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 855 days.

(21) Appl. No.: 17/050,303

(22) PCT Filed: Apr. 23, 2019

(86) PCT No.: PCT/EP2019/060368
§ 371 (c)(1),
(2) Date: Oct. 23, 2020

(87) PCT Pub. No.: WO2019/206909
PCT Pub. Date: Oct. 31, 2019

(65) Prior Publication Data
US 2021/0163474 A1 Jun. 3, 2021

(30) Foreign Application Priority Data
Apr. 24, 2018 (EP) .................................... 18169052

(51) Int. Cl.
*C07D 471/04* (2006.01)
(52) U.S. Cl.
CPC .................................. *C07D 471/04* (2013.01)
(58) Field of Classification Search
CPC ............. C07D 471/04; A61K 31/4375; C07B 2200/07
(Continued)

(56) References Cited

U.S. PATENT DOCUMENTS 5,037,987 A 8/1991 Herrmann et al.
2010/0136142 A1 6/2010 Baerfacker
(Continued)

FOREIGN PATENT DOCUMENTS

CA 2995905 A1 * 3/2017 ......... A61K 31/4375
CN 101648903 A 2/2010
(Continued)

OTHER PUBLICATIONS

Omkar , Omkar Specialty Chemicals LTD, 2015, p. 1-2). (Year: 2015).*
(Continued)

*Primary Examiner* — Taylor V Oh
(74) *Attorney, Agent, or Firm* — Quarles & Brady LLP

(57) ABSTRACT

The present invention relates to a novel and improved process for preparing (4S)-4-(4-cyano-2-methoxyphenyl)-5-ethoxy-2,8-dimethyl-1,4-dihydro-1,6-naphthyridine-3-carboxamide of the formula (I)
(Continued)

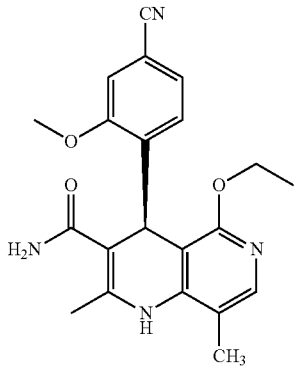

(I)

and also to the preparation of the enantiomer (Ia) by racemate resolution using chiral substituted tartaric acid esters of the general formulae (IIIa) and (IIIb)

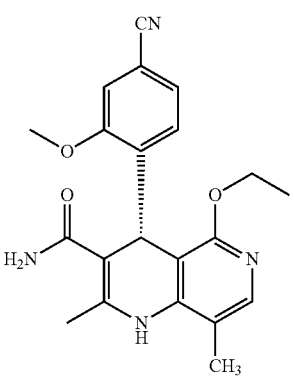

(Ia)

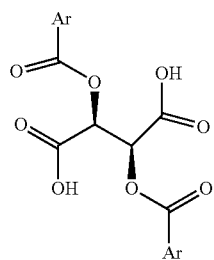

(IIIa)

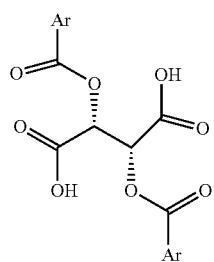

(IIIb)

where Ar represents a substituted or unsubstituted aromatic or heteroaromatic radical.

34 Claims, 1 Drawing Sheet

(58) Field of Classification Search
USPC .......................................................... 546/123
See application file for complete search history.

(56) References Cited

U.S. PATENT DOCUMENTS

| 2018/0244670 A1 | 8/2018 | Platzek |
| 2019/0127369 A1 | 5/2019 | Platzek |

FOREIGN PATENT DOCUMENTS

| CN | 101798280 A | 8/2010 |
| JP | 2008521887 A | 6/2008 |
| WO | 2006059886 A1 | 6/2006 |
| WO | 2008104306 A2 | 9/2008 |
| WO | 2016016287 A1 | 2/2016 |
| WO | 2017032673 A1 | 3/2017 |
| WO | 2017032678 A1 | 3/2017 |

OTHER PUBLICATIONS

Bärfacker L. et al. (2012). "Discovery of BAY 94-8862: A Nonsteroidal Antagonist of the Mineralocorticoid Receptor for the Treatment of Cardiorenal Diseases," ChemMedChem 7:1385-1403.
European Electronic Search Report mailed Jun. 15, 2018 for European Application No. EP18169052 filed Apr. 24, 2018, 114 pages.
International Search Report mailed Jun. 18, 2019 for PCT Application No. PCT/EP2019/060368, filed Apr. 23, 2019, 4 pages.
Paredes G. et al. (2007). "Optimization of simulated moving bed and col. chromatography for a plasmid DNA purification step and for a chiral separation," Journal of Chromatography A 1142: 56-68.
Stahl, P.H. et al., Eds. (2008). Handbook of Pharmaceuticals Salts, Properties, Selection, and Use, p. 166.
Subramani H.J. et al. (2003). "Optimization of reactive SMB and Varicol systems," Computers and Chemical Engineering 27: 1883-1901.
Synoradzki L. et al. (2008). "Tartaric Acid and Its O-Acyl Derivatives. PART2. Application of Tartaric Acid and of O-Acyltartaric Acids and Anhydrides. Resolution of Racemates," The New Journal for Organic Synthesis 40(2): 163-200.
Written Opinion of the International Search Authority mailed Jun. 18, 2019 for PCT Application No. PCT/EP2019/060368, filed Apr. 23, 2019, 7 pages.

* cited by examiner

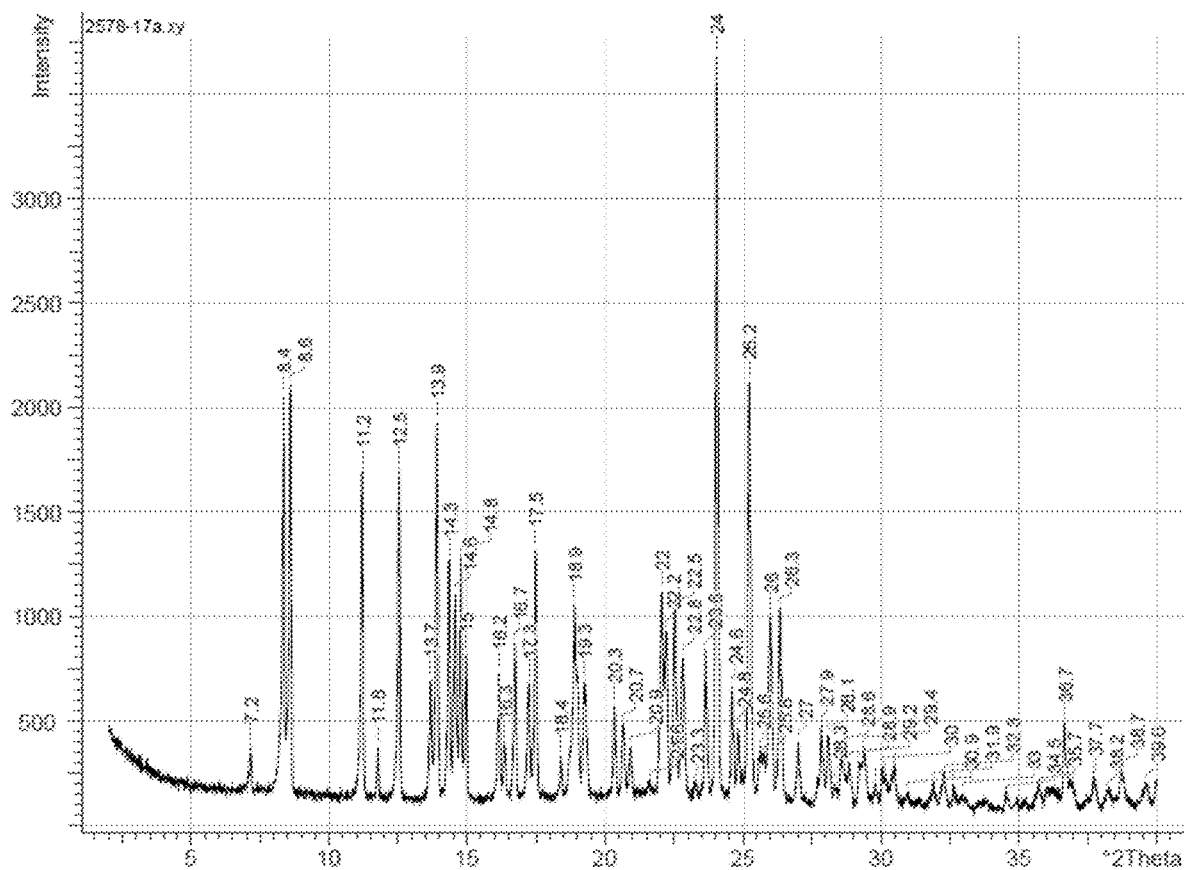

US 12,054,481 B2

METHOD FOR THE PREPARATION OF (4S)-4-(4-CYANO-2-METHOXYPHENYL)-5-ETHOXY-2,8-DIMETHYL-1,4-DIHYDRO-1-6-NAPHTHYRIDINE-3-CARBOX-AMIDE BY RACEMATE SEPARATION BY MEANS OF DIASTEREOMERIC TARTARIC ACID ESTERS

CROSS REFERENCE TO RELATED APPLICATIONS

This application is a national stage application under 35 U.S.C § 371 of International Application No. PCT/EP2019/060368, filed internationally on Apr. 23, 2019, which claims the benefit of priority to European Application No. 18169052.0, filed Apr. 24, 2018.

The present invention relates to a novel and improved process for preparing (4S)-4-(4-cyano-2-methoxyphenyl)-5-ethoxy-2,8-dimethyl-1,4-dihydro-1,6-naphthyridine-3-carboxamide of the formula (I)

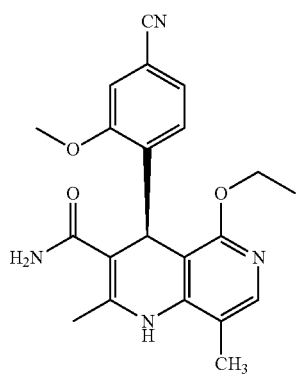

(I)

and also to the preparation of the enantiomer (Ia) by racemate resolution using chiral substituted tartaric acid esters of the general formulae (IIIa) and (IIIb)

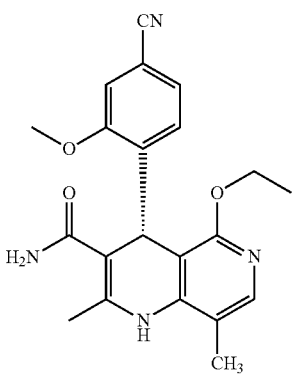

(Ia)

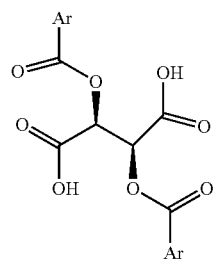

(IIIa)

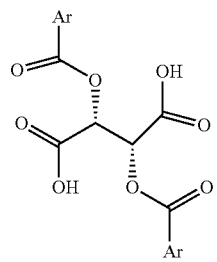

(IIIb)

where Ar represents a substituted or unsubstituted aromatic or heteroaromatic radical. Finerenone (I) acts as a non-steroidal antagonist of the mineralocorticoid receptor and may be used as an agent for prophylaxis and/or treatment of cardiovascular and renal disorders such as heart failure and diabetic nephropathy, for example.

The compound of the formula (I) and their preparation process are described in WO 2008/104306 and ChemMedChem 2012, 7, 1385, and also in WO 2016/016287 A1. To obtain the compound of the formula (I), the racemic mixture of the amides (II)

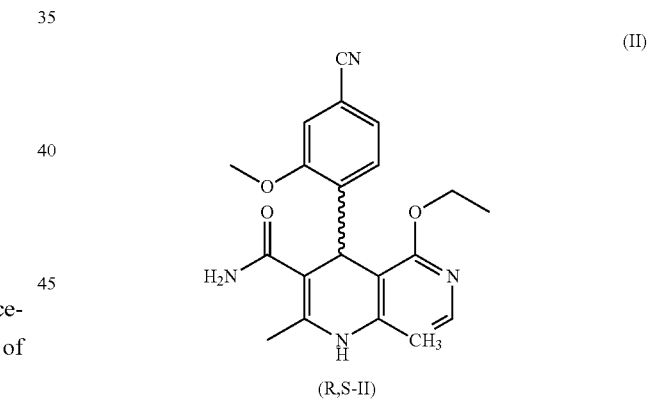

(II)

(R,S-II)

has to be separated into the enantiomers since only the enantiomer of the formula (I) is active.

In the published research scale synthesis (WO 2008/104306), a specifically synthesized chiral phase was used for this purpose (prepared in-house), which comprised poly(N-methacryloyl-D-leucine-dicyclopropylmethylamide as chiral selector. It has been found that the separation can also be performed on a readily commercially available phase. This takes the form of the phase Chiralpak AS-V, 20 μm. The eluent used was a mixture of methanol/acetonitrile 60:40. In this case, the chromatography may be carried out on a conventional chromatography column, but preferably the techniques known to those skilled in the art such as SMB (simulated moving bed; G. Paredes, M. Mazotti, Journal of Chromatography A, 1142 (2007): 56-68) or Varicol (Computers and Chemical Engineering 27 (2003) 1883-1901) are used.

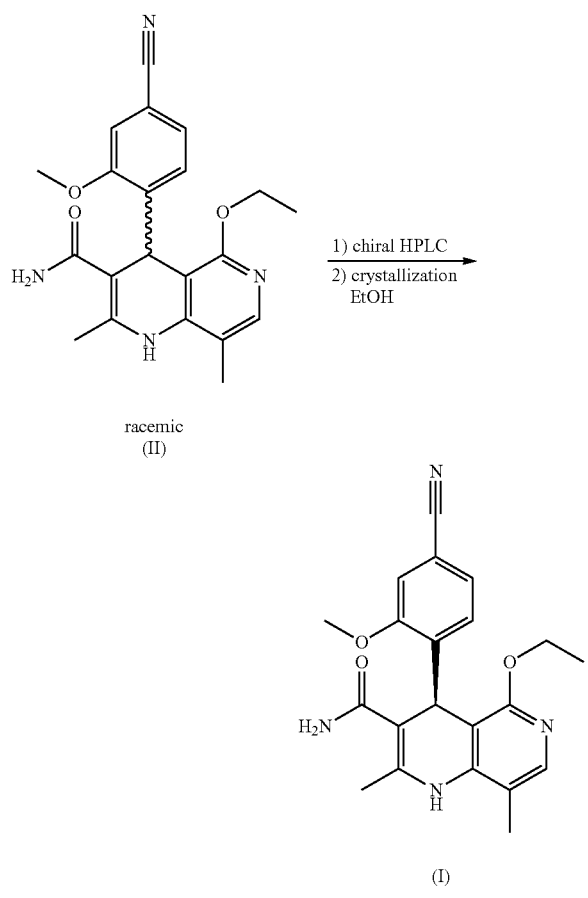

Although SMB separation affords a relatively good yield and optical purity, the acquisition costs and the operation of such a facility under GMP conditions poses a great challenge and is associated with high costs. The respective chiral phase employed, too, is very expensive and has only a limited life span and has to be frequently replaced during continuous production. For reasons of production engineering, this is not optimal unless there is a second plant present to ensure continuous operation, which is associated with additional costs. Furthermore, especially in the case of products produced on a ton scale, solvent recovery is the time-limiting step and requires the acquisition of gigantic falling-film evaporators and is associated with the consumption of huge amounts of energy.

Accordingly, it was an object to search for alternatives for separating the enantiomer mixture, which alternatives are significantly more cost-effective and can be carried out using conventional pilot plant equipment (stirred vesselisolation apparatuses). Such facilities are traditionally standard equipment of pharmaceutical production plants and do not require additional investments. Moreover, qualification and validation of batch processes is considerably easier than that of chromatographic processes, which is an additional advantage.

Numerous attempts were carried out to develop a separation using the classic methods of racemate resolution (variation of chiral organic acid and solvent), as shown in Table 1:

TABLE 1

| Acid | Solvent |
|---|---|
| (S)-(+)-1,1-binaphthyl-2,2-diyl hydrogenphosphate | methanol |
| (−)-quinic acid | ethanol |
| (−)-O,O'-diacetyl-L-tartaric acid | 1-propanol |
| (−)-O,O'-dipivaloyl-L-tartaric acid | 2-propanol |
| (+)-3-bromocamphor-10-sulfonic acid | 1-butanol |
| (+)-4-chlorotartranilic acid | isobutanol |
| (+)-4'-nitrotartranilic acid | 1-pentanol |
| (+)-camphoric acid | cyclohexanol |
| (+)-O-acetyl-L-mandelic acid | benzyl alcohol |
| (1R)-(−)-camphor-10-sulfonic acid | acetone |
| (1S)-(−)-camphanic acid | ethylene glycol |
| (2R,3R)-(+)-tartaric acid | chlorobenzene |
| (R)-(+)-alpha-methoxy-alpha-trifluoromethylphenylacetic acid | dichloromethane |
| (S)-(−)-2-bromopropionic acid | ethyl acetate |
| (S)-(−)-2-chloropropionic acid | dimethylacetamide |
| (S)-(+)-citramalic acid | THF |
| (S)-(+)-mandelic acid | toluene |
| Ac-acid triple mix | toluene/ethyl acetate 95:5 |
| malic acid | toluene/ethyl acetate 90:10 |
| chlocyphos | toluene/ethyl acetate 80:20 |
| D-(+)-HPP monoacid | toluene/ethyl acetate 50:50 |
| L-glutaminic acid | toluene/ethanol 95:5 |
| L-lactic acid | methanol/water 90:10 |
| menthoxyacetic acid | methanol/water 80:20 |
| N-(3,5-dinitrobenzoyl)-(R)-(−)-2-phenylglycine | methanol/water 50:50 |
| N-acetyl-L-leucine | ethyl acetate/MeOH 90:10 |
| N-acetyl-L-phenylalanine | ethanol/water 90:10 |
| N-Ac-proline-OH | ethanol/water 85:15 |
| naproxen | ethanol/water 80:20 |
| phencyphos | ethanol/water 75:25 |
| | ethanol/water 70:30 |
| | ethanol/water 50:50 |

TABLE 1-continued

| Acid | Solvent |
|---|---|
| | methanol/water 90:10 |
| | methanol/water 80:20 |
| | methanol/water 50:50 |
| | 1-propanol/water 80:20 |
| | isopropanol/water 80:20 |
| | 1-butanol/water 90:10 |
| | 2-butanol/water 80:20 |
| | 2-butanol/water 90:10 |
| | 1-pentanol/water 90:10 |
| | cyclohexanol/water 90:10 |
| | benzyl alcohol/water 90:10 |
| | ethylene glycol/water 80:20 |

Inter alia, we also carried out experiments with the classic resolving agent (+)-tartaric acid.

However, in none of the cases salt formation was observed; instead, in each case only the racemate precipitates from the solution, without having formed a salt. This corresponds essentially to the expectations of the person skilled in the art which can be derived from the pKs of molecule (II), i.e. that classic racemate resolution by diastereomer salt formation with organic acids should not be possible since the measured pKs (for the base) is at 4.3, which virtually excludes salt formation, so that salt formation would only be possible using preferably very strong inorganic or organic mineral acids such as chiral sulfonic acids or phosphonic acids. According to the literature, for example "Handbook of Pharmaceutical Salts—Properties, Selection and Use; by P. Heinrich Stahl, Camille G. Wermuth (Eds.); Wiley-VCH, p. 166", the pK difference should be at least 3 pK units to allow stable salt formation. Indeed, this is found using, for example, the cyclic phosphoric ester chlocyphos below:

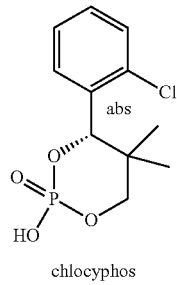

chlocyphos

The reaction of 3 eq. of this cyclic phosphoric ester with the racemate (II) gives a diastereomeric salt in which (I) is present with an enantiomeric excess of only 44% e.e.

All efforts to push the enantiomeric excess towards >99% e.e. were unsuccessful; in addition, chlocyphos was not commercially available in large amounts; accordingly, we investigated other alternatives.

No salt formation was observed in reactions with alkyl-substituted tartaric acid derivatives such as (−)-O,O'-dipivaloyl-L-tartaric acid or (−)-O,O'-diacetyl-L-tartaric acid.

On further investigation of the subject, we found, surprisingly, that aromatically or heteroaromatically substituted derivatives of tartaric acid are highly suitable for forming "diastereomeric salts" from racemate (II).

Accordingly, the present application provides the racemate resolution of (II)

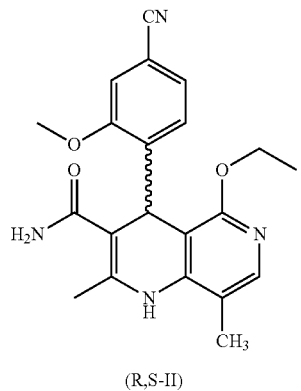

(R,S-II)

into (Ia) and/or (1)

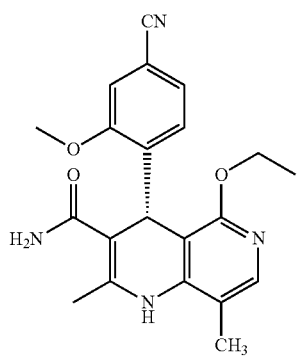

(Ia)

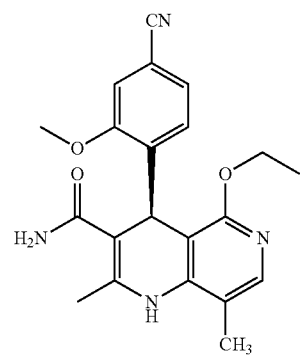

(I)

using chiral substituted tartaric esters of the general formulae (IIIa) or (IIIb)

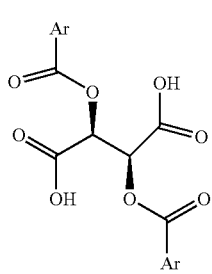
(IIIa)

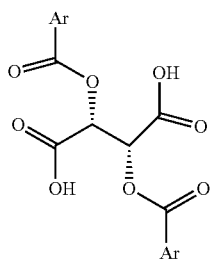
(IIIb)

where Ar represents an unsubstituted or substituted aromatic or heteroaromatic radical.

The invention further provides processes for preparing (4S)-4-(4-cyano-2-methoxyphenyl)-5-ethoxy-2,8-dimethyl-1,4-dihydro-1,6-naphthyridine-3-carboxamide of the formula (I)

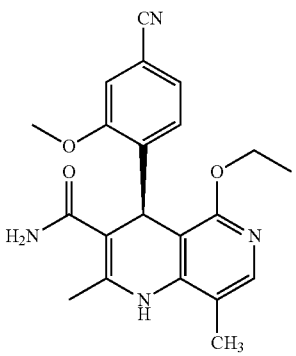
(I)

by racemate resolution of (II)

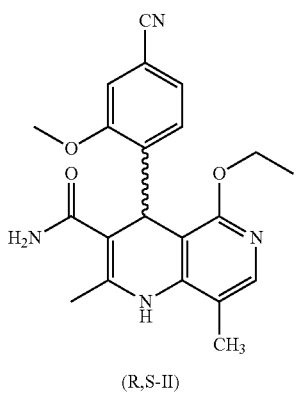 [SMILES: CCOc1ncc(C)c2c1C(c1ccc(C#N)cc1OC)C(C(N)=O)=C(C)N2]
(R,S-II)

using a chiral substituted tartaric ester of the formula (IIIa)

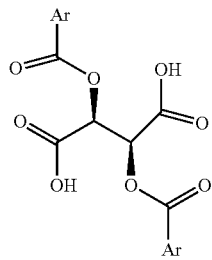
(IIIa)

where Ar represents an unsubstituted or substituted aromatic or heteroaromatic radical.

DESCRIPTION OF THE FIGURE

FIG. 1: XRPD of compound (VI) obtained as a colourless crystalline powder according to Example I.a.

The term "substituted" means that one or more hydrogen atoms on the atom or group in question has/have been replaced by a selection from the group specified, with the proviso that the normal valency of the atom in question is not exceeded under the circumstances present. Combinations of substituents and/or variables are permissible.

The term "unsubstituted" means that none of the hydrogen atoms have been replaced.

The heteroaryl group or the heteroaromatic radical may be a 5-membered heteroaryl group, for example thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, for example pyridinyl, pyridazinyl, pyrimidinyl, pyrazinyl or triazinyl; or a tricyclic heteroaryl group, for example carbazolyl, acridinyl or phenazinyl; or a 9-membered heteroaryl group, for example benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, for example quinolinyl, quinazolinyl, isoquinolinyl, cinnolinyl, phthalazinyl, quinoxalinyl or pteridinyl.

The heteroaryl group is in particular a pyridinyl, pyrazinyl, pyrrolyl, pyrazolyl or pyrimidinyl group.

For the purposes of the present application, an aryl group is in particular a phenyl group.

Suitable substituents for the purposes of the present invention are halogen, $C_1$-$C_6$-alkyl, $C_1$-$C_6$-alkoxy, nitrile, a nitro group, cyano group, CF3 group or amide group such as, for example, NHCOR in which R represents methyl, ethyl or phenyl, or a —NRCOR group in which R has the meaning mentioned above, or a CONHR group in which R has the meaning mentioned above, or a CONRR' group in which R' has the same meaning as R as defined above, or cyclic amides such as the —CO-morpholine radical or the —CO-piperidine radical.

The term "halogen atom" refers to a fluorine, chlorine, bromine or iodine atom, preferably a fluorine, chlorine or bromine atom.

The term "$C_1$-$C_6$-alkyl" denotes a straight-chain or branched saturated monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2- dimethylpropyl, neopentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group or an isomer thereof. The group has in particular 1, 2, 3 or 4 carbon atoms ("$C_1$-$C_4$-alkyl"), e.g. a methyl, ethyl, propyl, isopropyl, butyl, see-butyl, isobutyl or tert-butyl group, in particular 1, 2 or 3 carbon atoms ("$C_1$-$C_3$-alkyl"), e.g. a methyl, ethyl, n-propyl or isopropyl group.

The term "$C_1$-$C_6$-alkoxy" denotes a straight-chain or branched saturated monovalent group of the formula ($C_1$-$C_6$-alkyl)-O— in which the term "$C_1$-$C_6$-alkyl" is as defined above, e.g. a methoxy, ethoxy, n-propoxy, isopropoxy, n-butoxy, see-butoxy, isobutoxy, tert-butoxy, pentyloxy, isopentyloxy or n-hexyloxy group or an isomer thereof.

Preferably, Ar represents:

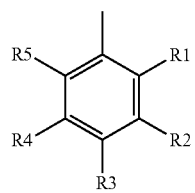

where R1, R2, R3, R4, R5 each represent a hydrogen atom or an alkyl radical such as, for example, methyl, ethyl, propyl, or a halogen atom such as, for example, fluorine, chlorine, bromine or iodine, or an ether group such as, for example, O-methyl, O-ethyl, O-phenyl, or a nitro group, cyano group, CF3 group or amide group such as, for example, NHCOR in which R may represent methyl, ethyl or phenyl, or a —NRCOR group in which R has the meaning mentioned above, or a CONHR group in which R has the meaning mentioned above, or a CONRR' group in which R' has the same meaning as R as defined above, or represent cyclic amides such as the —CO-morpholine radical or the —CO-piperidine radical. The substitution patterns may differ widely; thus, up to 5 different substituents are theoretically possible, but preference is generally given to the monosubstituted Ar radicals. However, Ar may also be a substituted heteroaromatic radical such as, preferably, pyridine or pyrazine. It may also be a polycyclic aromatic hydrocarbon such as a substituted naphthalene, anthracene or quinoline.

Particularly preferred Ar are:

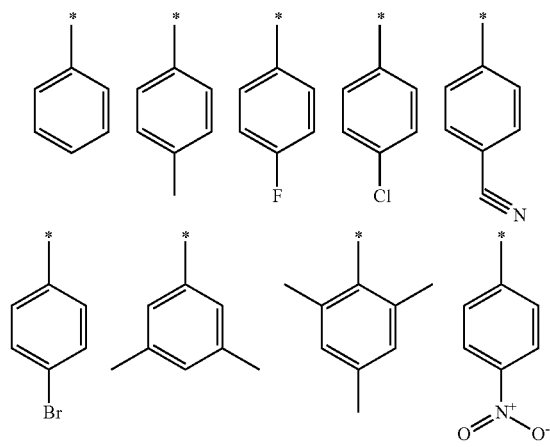

-continued

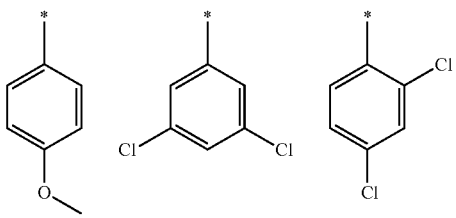

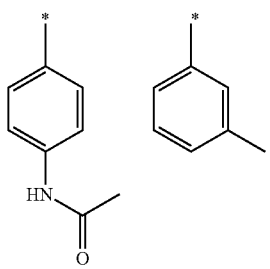

where * represents the point of attachment.

With particular preference, Ar represents:

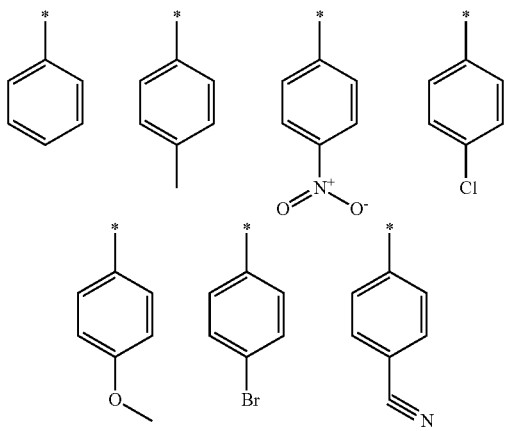

where * represents the point of attachment.

Very particularly preferred Ar radicals are:

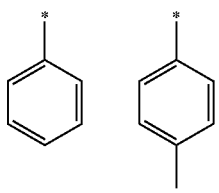

where * represents the point of attachment.

Of these, the unsubstituted ring (phenyl) is especially preferred.

The preparation of the tartaric esters is known from the literature, as described, for example, in Organic Synthesis, Coll. Vol. 9, p. 722 (1998); Vol. 72, p. 86 (1995), and in Chirality 2011 (23), 3, p. 228.

The invention furthermore relates to diastereomeric salts of the formulae

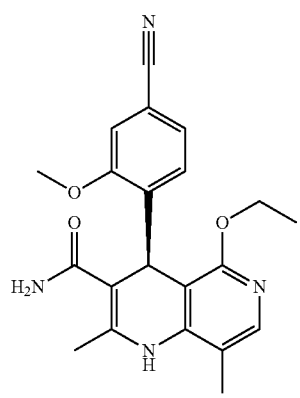

(IV a)

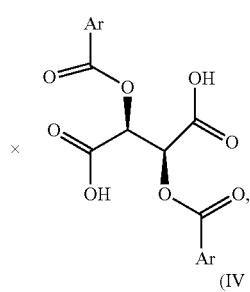

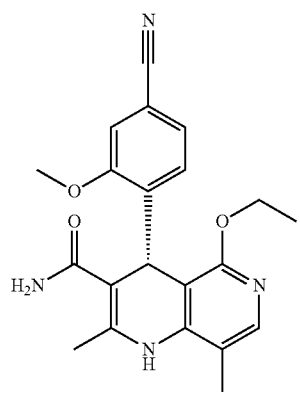

(IV b)

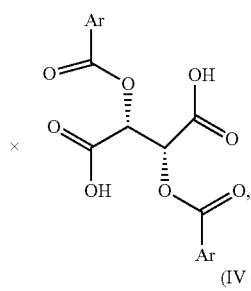

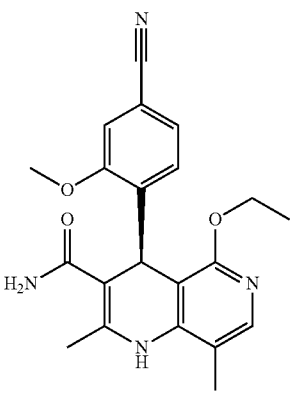

(IV c)

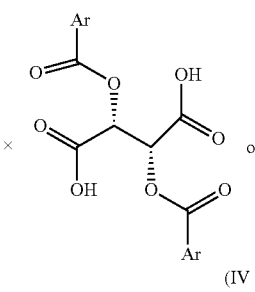

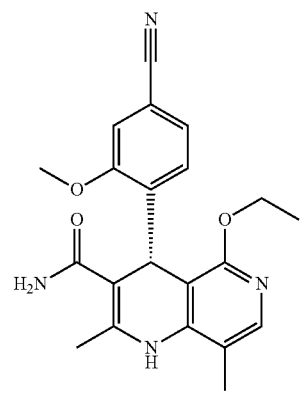

(IV d)

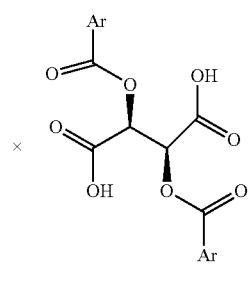

in which Ar represents an unsubstituted or substituted aromatic or heteroaromatic radical and has the meaning given above.

Particular preference is given to diastereomeric salts in which Ar represents phenyl.

Whether this is really a classic diastereomeric salt or a molecular 1:1 complex stabilized by hydrogen bonds cannot be predicted with certainty. What is clear is that these molecular 1:1 aggregates are highly stable, behave like classic diastereomeric salts and can be isolated; so hereinbelow we still use the term diastereomeric salts. For the preparation of the diastereomeric salts, tartaric acid derivatives of the general formulae (IIIa) and (IIIb) are used:

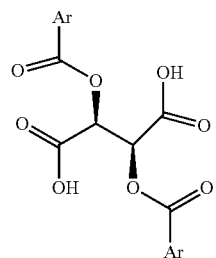

(IIIa)

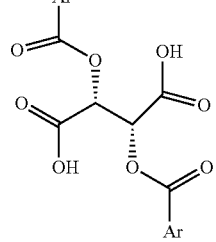

(IIIb)

where Ar represents a substituted or unsubstituted aromatic or heteroaromatic radical.

The preparation of the diastereomeric salts is carried out as follows:

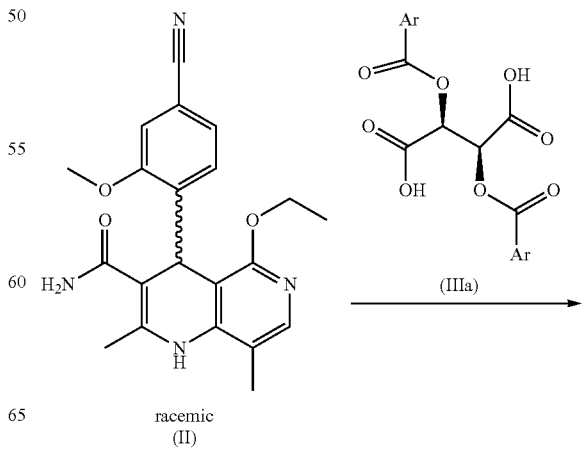

racemic
(II)

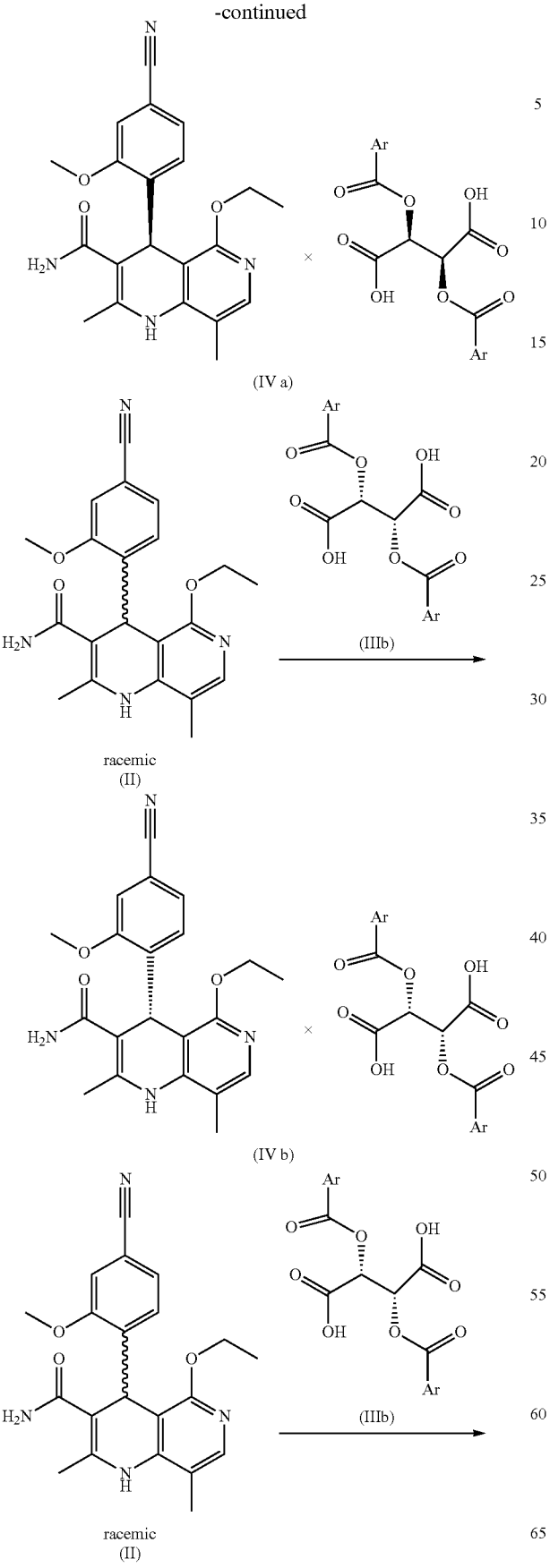
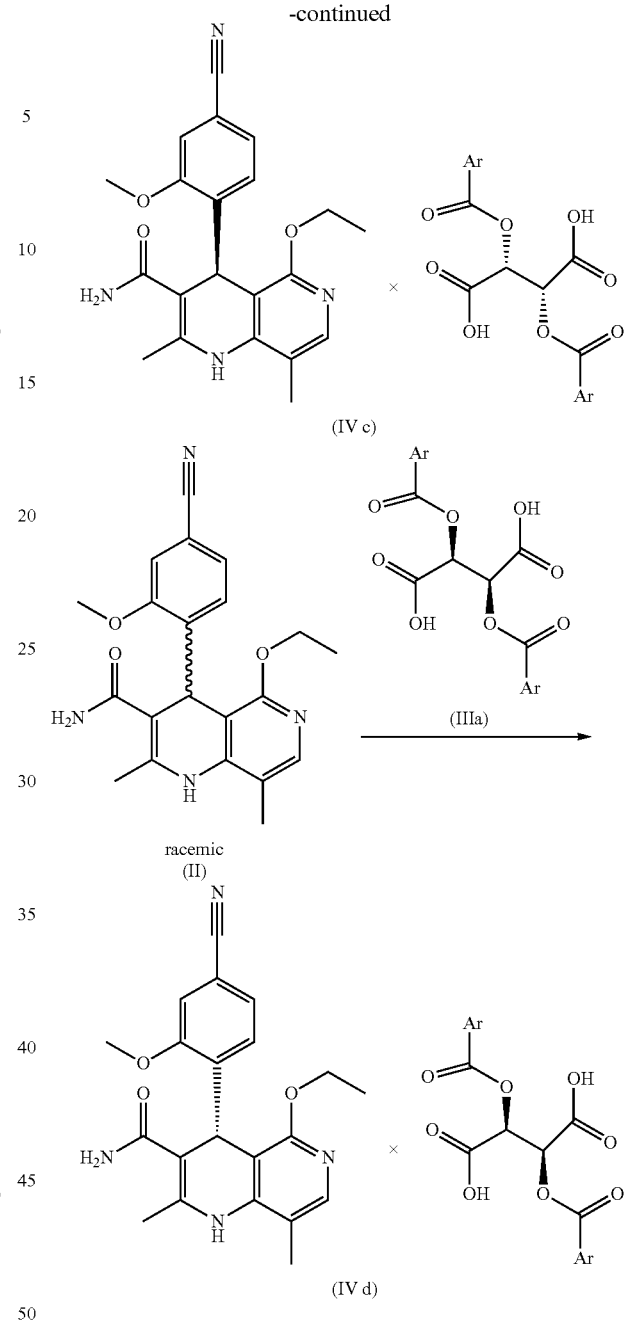

The reaction of the racemic mixture (II) with a tartaric acid derivative of the general formula (IIIa) or (IIIb) yields 4 possibilities of diastereomeric salt formation (IV a-d). Surprisingly, a certain preference is observed such that, if, for example, rac-(II) is reacted with a tartaric acid derivative of the general formula (IIIa), in most cases the diastereomeric salt of the general formula (IVa) is obtained, with the enantiomer having the S configuration preferably forming the salt. Nearly quantitatively, the diastereomeric salt (IVa) precipitates from the solution from which it can then be isolated e.g. by filtration, the enantiomer having the R configuration remaining in solution. In a very similar manner, the mirror-image salt of the general formula (IVb) is prepared by reacting the racemate (II) with the tartaric acid derivative of the general formula (IIIb), with the enantiomer having the R configuration preferably forming the salt. The precipitated diastereomeric salts can be separated off nearly quantitatively, and here the S-enantiomer remains in solution.

Via the stoichiometric ratio of (II) to (IIIa) and (IIIb), respectively, and by the selection of solvent, yield and enantiomeric purity can be optimized.

Since finerenone (I) has the S configuration, the S,S-configured tartaric acid derivatives are preferably used for racemate resolution since in this case the diastereomeric salt of the S-enantiomer is formed with preference.

For racemate resolution, 0.4 to 1.2 eq. of tartaric ester (IIIa) or (IIIb) are employed, preferably 0.4 to 0.7 eq., particularly preferably 0.45 to 0.6 eq., very particularly preferably 0.50-0.55 eq.

The formation of diastereomeric salts takes place in solvent mixtures consisting of water and water-miscible organic solvents.

For the purposes of the application, suitable organic solvents are, for example, ethanol, methanol, isopropanol, 1-propanol, ethyl acetate, isobutanol, dichloromethane, 1-pentanol or acetone; however, preference is given to using ethanol. The solvents can also be employed in the commercially available denatured form, such as the denaturing agents usually employed for ethanol, e.g. toluene, methyl ethyl ketone, thiophene, hexane, which has great economic advantages; accordingly, in particular for industrial scale use, spirits may be used which, for the purposes of the application, consist of ethanol optionally denatured with toluene or methyl ethyl ketone. Accordingly, for the purposes of the present application, if mention is made hereinbelow of ethanol as solvent, this is to be understood to mean, in addition to pure ethanol, also spirits in the sense of the above definition, in particular for industrial scale use. In addition, use was also made of the following solvents: ethyl acetate/methanol 90:10; methanol/water 80:20; ethanol/water 90:10; ethanol/water 85:15; ethanol/water 80:20; ethanol/water 75:25; ethanol/water 70:30; dichloromethane; 1-propanol/water 80:20; 1-pentanol; 1-pentanol/water 90:10; isopropanol; isopropanol/water 80:20; isobutanol/water 90:10; isobutanol/water 80:20; cyclohexanol/water 90:10; benzyl alcohol/water 90:10; ethylene glycol; ethylene glycol/water 80:20.

Preferably, the racemate resolution is carried out in an ethanol/water mixture, the mixtures (v/v) being in the range of ethanol:water=1:1 to 6:1. However, preference is given to a mixture of ethanol:water=4:1 to 3:1. Particular preference is given to a mixture of ethanol:water=3:1. The mixture can be prepared beforehand or else be produced in situ, once all the components have been charged into a pot. The solvent mixture can be employed in an excess of from 10- to 40-fold, based on the racemate (II), e.g. 10 l to 40 l of solvent mixture are employed per 1 kg of racemate. Preference is given to a 10- to 20-fold excess, in particular a 13- to 16-fold excess—particular preference is given to a 14- to 15-fold excess.

Usually, the racemate resolution is carried out by initially charging all components into the solvent mixture at room temperature, then heating to 60 to 80° C., but preferably to 75° C., stirring at 75° C. for 2 to 10 hours, preferably 3 to 4 hours, and then cooling to room temperature (about 20 to 23° C.) over 3 to 10 hours, preferably 4 to 5 hours (using a temperature ramp). The mixture is then allowed to stir at room temperature for another 2 to 24 hours, preferably 5 to 18 hours, particularly preferably 12 to 16 hours. Racemate resolution is preferably carried out at a temperature of 75° C.

Subsequently, the precipitated diastereomeric salt (IVa), (IVb), (IVc) and/or (IVd) is isolated.

The isolation is carried out by methods known to the person skilled in the art, for example by filtration or using a centrifuge. The filter cake obtained in this manner can be washed once or several times with a solvent or solvent mixture. This is followed by drying under reduced pressure, preferably <100 mbar, at elevated temperature (50 to 80° C., preferably 50° C.). In some cases, the use of a carrier gas has been found to be advantageous.

Using the procedure described above, it is possible to prepare diastereomeric salts of very high chemical purity. The enantiomeric excess of the diastereomeric salts is generally >97% e.e. (see examples) The diastereomeric salts do not have to be dried necessarily but may also be employed moist in the next process stage.

In addition to the customary procedure mentioned above, the process steps may also be combined or their sequence may be changed, as shown in Table 2 below:

TABLE 2

| 1st Step | 2nd Step | 3rd Step | 4th Step | 5th Step |
| --- | --- | --- | --- | --- |
| initial charging of racemate (II) and diaryltartaric acid (IIIa or b) | addition of ethanol | addition of water | heating | |
| initial charging of racemate (II) | addition of ethanol | addition of diaryltartaric acid (IIIa or b) | addition of water | heating |
| initial charging of racemate (II) | addition of water | addition of diaryltartaric acid (IIIa or b) | addition of ethanol | heating |
| initial charging of diaryltartaric acid (IIIa or b) | addition of ethanol | addition of racemate (II) | addition of water | heating |
| initial charging of diaryltartaric acid (IIIa or b) | addition of water | addition of racemate (II) | addition of ethanol | heating |
| initial charging of racemate (II) and diaryltartaric acid (IIIa or b) | addition of the ethanol/water mixture | heating | | |
| initial charging of racemate (II) | addition of the ethanol/water mixture | addition of diaryltartaric acid (IIIa or b) | addition of ethanol | heating |

TABLE 2-continued

| 1st Step | 2nd Step | 3rd Step | 4th Step | 5th Step |
|---|---|---|---|---|
| initial charging of diaryltartaric acid (IIIa or b) | addition of the ethanol/water mixture | addition of racemate (II) | addition of water | heating |
| initial charging of the ethanol/water mixture | addition of racemate (II) | addition of diaryltartaric acid (IIIa or b) | heating | |
| initial charging of the ethanol/water mixture | addition of diaryltartaric acid (IIIa or b) | addition of racemate (II) | heating | |
| initial charging of ethanol | addition of racemate (II) | addition of water | addition of diaryltartaric acid (IIIa or b) | heating |
| initial charging of water | addition of racemate (II) | addition of ethanol | addition of diaryltartaric acid (IIIa or b) | heating |
| initial charging of ethanol | addition of diaryltartaric acid (IIIa or b) | addition of water | addition of racemate (II) | heating |
| initial charging of water | addition of diaryltartaric acid (IIIa or b) | addition of ethanol | addition of racemate (II) | heating |

Depending on the type of plant in the pilot plant or in the production, one variant or the other may be advantageous.

In the next step, the diastereomeric salt is treated with a base and the solvent is removed. Removal of the solvent is carried out using methods known to the person skilled in the art, for example removal by distillation. To produce the chiral compounds (I) and (Ia), the diastereomeric salt of the general formula (IVa), (IVb), (IVc) or (IVd) has to be treated with a base, following distillative removal of the organic solvent, the target molecule (I) or (Ia) then precipitates from the solution and is isolated—for example by filtration and washing—and the respective tartaric ester according to formula (IIIa) or (IIIb) then remains in solution in the form of a salt.

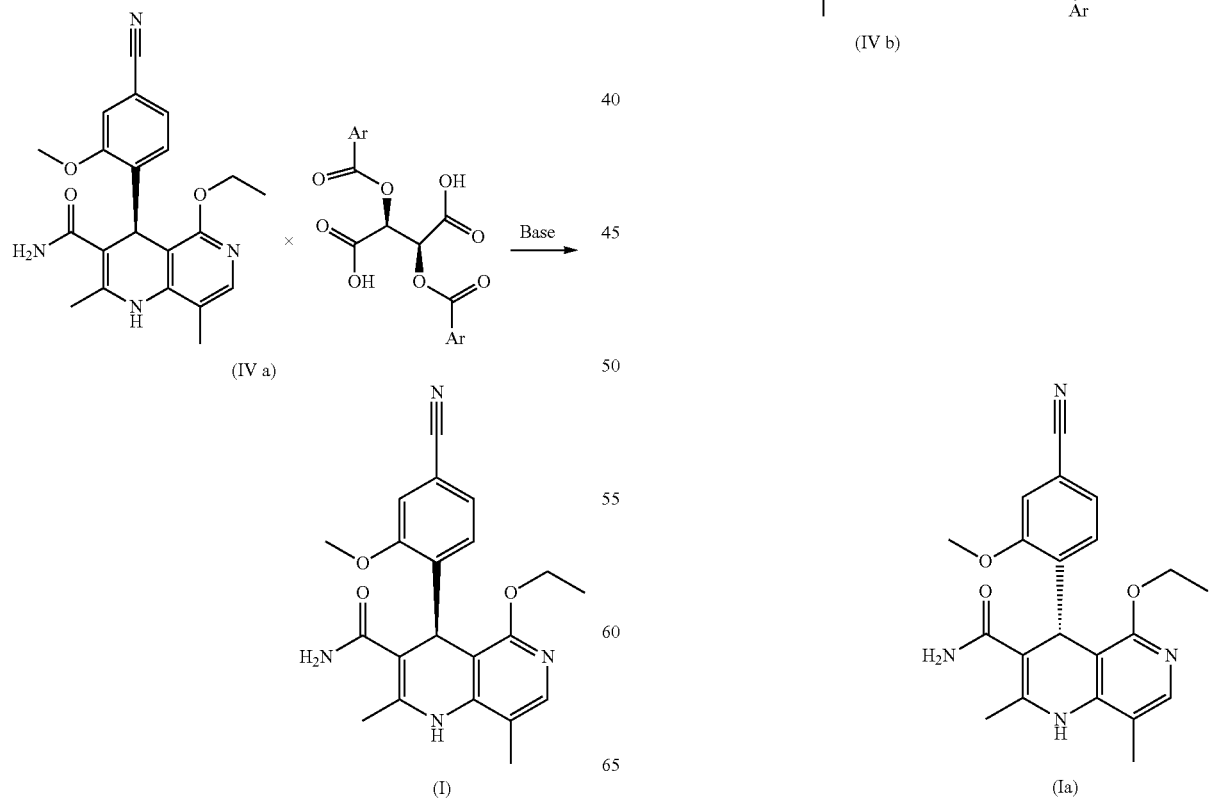

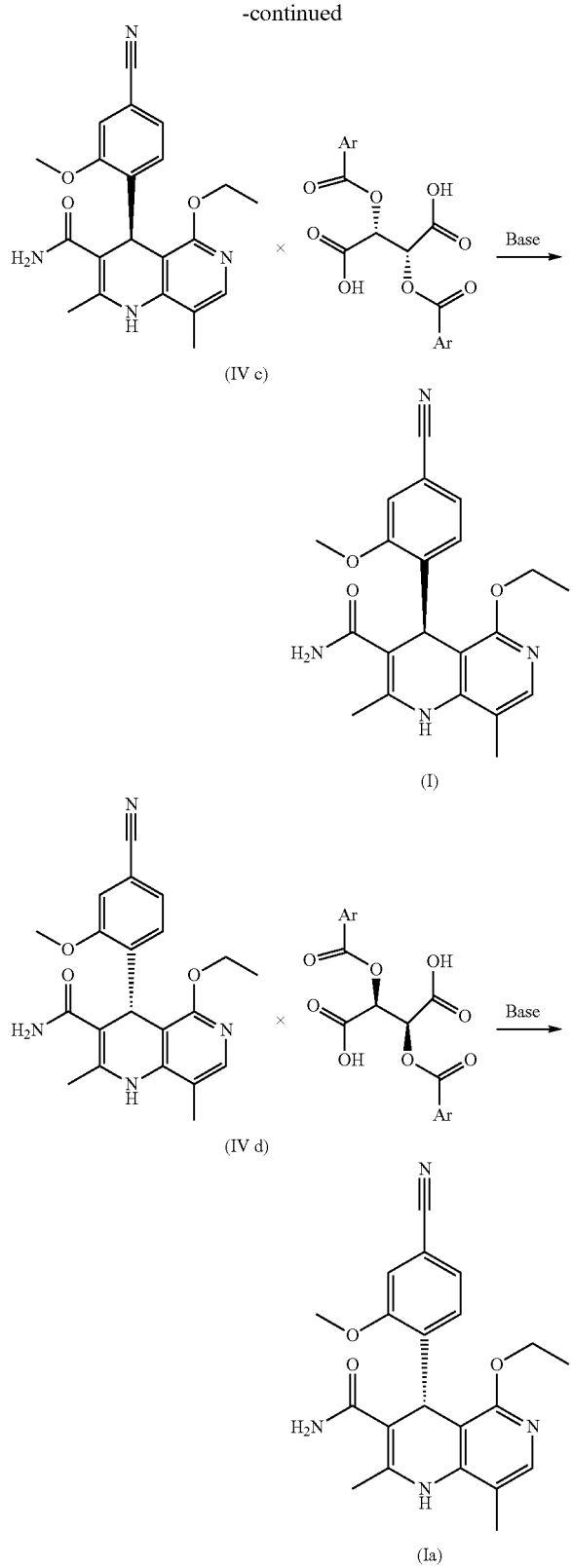

sodium bicarbonate, potassium bicarbonate, sodium phosphate, potassium phosphate, ammonium phosphate may be employed as inorganic bases. However, preference is given to using sodium hydroxide, sodium phosphate or potassium phosphate. Particular preference is given to using sodium phosphate or potassium phosphate.

It is important to emphasize that the inorganic bases can be employed both in anhydrous form and in the form of their hydrates; thus, for example, sodium phosphate (anhydrous) and sodium phosphate hydrate may be used successfully. Aliphatic or aromatic bases such as triethylamine, imidazole, N-methylimidazole, Hunig base, pyridine, 1,8-diazabicyclo[5.4.0]undec-7-ene (DBU) may be employed as organic base.

Release of the target compound (I) or (Ia) takes place in mixtures of water, water-miscible organic solvents such as ethanol, isopropanol, 1,2-ethanediol, methoxyethanol, methanol or acetone; however, preference is given to using ethanol. The solvents may also be employed in the commercially available denatured form, such as the denaturing agents employed for ethanol, e.g. toluene, methyl ethyl ketone, thiophene, hexane, preferably, spirits may be used which, for the purposes of the application, consist of ethanol optionally denatured with toluene or methyl ethyl ketone, which has great economic advantages. It has been found to be advantageous to use mixtures of water and ethanol, with mixtures (v/v) in the range of ethanol:water=1:6 to 1:3. However, preference is given to a mixture of ethanol:water=1:4. The mixture can be prepared beforehand or else be produced in situ, once all the components have been charged into a pot. These mixtures may be used in an amount 7 to 20 times that of the diastereomeric salt (IVa or IVb or IVc or IVd) employed, i.e., for example, 1 kg in 7 l to 20 l of this mixture. Preferably, the amount of the mixture used is 8 to 12 times, particularly preferably 9 to 11 times, very particularly preferably 10 times the amount of the salt.

The target compound (I) or (Ia) is released by initially charging the diastereomeric salt (IVa or IVb or IVc or IVd) in a solvent mixture at from 0 to 80° C., preferably 20 to 50° C., followed by addition of the organic or inorganic base (either in solid form or as a solution, preferably in water) to adjust the pH to from 6.9 to 9.5, preferably from 7.0 to 8.0, particularly preferably to pH 7.5. Optionally, the base may be added very rapidly (over a few minutes) or else very slowly (over several hours), for example over 5 minutes to 3 hours. In any case, a more rapid addition is preferred; with preference, the metered addition is carried out over 5 min to 1 hour. For this purpose, use may be made of a pH meter installed in the reactor which checks the setting and slowly adds the base. However, it is also possible to initially add a fixed amount of base (solid or dissolved in a solvent) which, based on experience, ensures that the desired pH range is reached. In production, such a procedure is particularly preferred. It has been found to be advantageous to continue stirring, after the pH has been set, at 10 to 80° C., preferably 20 to 60° C., with preference 40-60° C. The additional stirring period may be from 1 to 10 hours, preferably 2-5 hours, particularly preferably 3-4 hours. The mixture is then allowed to cool to 15 to 25° C., e.g. using a ramp, and may then again be stirred for 1 to 64 hours (the 64 hours serve to demonstrate the robustness of the process, see Example 3b); however, the extra stirring time is preferably between 3 and 24 hours, and 10 to 20 hours are generally sufficient.

For the purposes of the present invention, suitable bases are inorganic and organic bases. Ammonia, aqueous sodium hydroxide solution, lithium hydroxide, potassium hydroxide, ammonium carbonate, sodium carbonate, potassium carbonate, lithium carbonate, ammonium bicarbonate, The isolation is carried out by methods known to the person skilled in the art, for example by filtration or using a centrifuge. The filter cake obtained in this manner can be washed once or several times with a solvent or solvent mixture. This is followed by drying under reduced pressure, preferably <100 mbar, at elevated temperature (50 to 80° C., preferably 50° C.). In some cases, the use of a carrier gas has been found to be advantageous.

However, it is also possible to dissolve the material obtained from the filter using ethanol or mixtures of water and ethanol and then, after adjustment of the amount of water/ethanol in the eluate, immediately proceed to the next process step (see below). This procedure is preferred in particular when working on an industrial scale as a drying step can be dispensed with.

Using the procedure described above, it is possible to prepare crude products of very high chemical purity. The enantiomeric excess of the crude products (I) and (Ia) is generally >96.5% e.e.

During up-scaling, it was found that complete removal of the tartaric esters (IIIa) and (IIb) from the crude products (I) and (Ia) is technically not always simple and that the content of these components is close to the specification limit. Since the specification requirements for the final active compound are very high (<0.1% (IIIa) in the final active compound), it has been found to be advantageous in some cases to add a further process step which ensures that the content of tartaric ester (IIIa) is reduced to below 0.15%, preferably below 0.1% and in particular below 0.05% and the final active compound is reproducibly obtained in a quality conforming to specifications. In the final crystallization yielding the pure product, the tartaric ester (IIIa) is hardly depleted, or virtually not at all, so that such a subsequent process step guarantees that robust operation of the entire process is ensured, moreover, the operation is virtually without loss. This process step, which ensures that compound (IIIa) is depleted to below 0.15%, preferably to below 0.1% and in particular to below 0.05% in the active compound, also forms part of the subject matter of the present invention. The process for reducing the amount of (IIIa) is carried out as follows. The starting material employed for the process is the dried or, advantageously, the still moist crude product of (I) or (Ia). Again, a base is used. Inorganic or organic bases may be employed for removing tartaric esters of the formula (IIIa) or (IIIb). Ammonia, aqueous sodium hydroxide solution, lithium hydroxide, potassium hydroxide, ammonium carbonate, sodium carbonate, potassium carbonate, lithium carbonate, ammonium bicarbonate, sodium bicarbonate, potassium bicarbonate, sodium phosphate, potassium phosphate, ammonium phosphate may be employed as inorganic bases. However, preference is given to using sodium hydroxide, sodium phosphate or potassium phosphate. Particular preference is given to using sodium phosphate or potassium phosphate. It is important to emphasize that the inorganic bases can be employed both in anhydrous form and in the form of their hydrates; thus, for example, sodium phosphate (anhydrous) and sodium phosphate hydrate may be used successfully. Aliphatic or aromatic bases such as triethylamine, imidazole, N-methylimidazole, Hunig base, pyridine, DBU may be employed as organic base.

Practice of the depletion of (IIIa) or (IIIb) is carried out in mixtures of water, with water-miscible organic solvents such as ethanol or isopropanol, 1,2-ethanediol, methoxyethanol, methanol, isopropanol or acetone; however, preference is given to using ethanol. The solvents may also be employed in the commercially available denatured form, such as the denaturing agents employed for ethanol, e.g. toluene, methyl ethyl ketone, thiophene, hexane, which has great economic advantages. It has been found to be advantageous to use mixtures of water and ethanol, with mixtures (v/v) in the range of ethanol:water=30:10 to 10:10. However, preference is given to a mixture of ethanol:water=20:10. The mixture can be prepared beforehand or else be produced in situ, once all the components have been charged into a pot. It is possible to use 10 to 20 times the amount of the solvent mixture, based on the diastereomeric salt (IVa), (IVb), (IVc) or (IVd) employed, i.e., for example, 1 kg in 10 l to 20 l of this mixture. Preferably, the amount of the mixture used is 10 to 14 times, particularly preferably 11 to 12 times, the amount of this mixture.

The practice of the depletion of (IIIa) or (IIIb) is carried out such that the mixture is initially charged in a solvent mixture as described above at from 40 to 80° C., preferably 50 to 70° C., followed by addition of the organic or inorganic base (either in solid form or as a solution, preferably in water) to adjust the pH to from 6.9 to 9.5, preferably from 7.5 to 9.0, particularly preferably to pH 8.5. Optionally, the base may be added very rapidly (over a few minutes) or else very slowly (over several hours), for example over 1 minute to 3 hours. In any case, a more rapid addition is preferred; with preference, the metered addition is carried out over 1 min to 1 hour. For this purpose, use may be made of a pH meter installed in the reactor which checks the setting and slowly adds the base. However, it is also possible to initially add a fixed amount of base (solid or dissolved in a solvent) which, based on experience, ensures that the desired pH range is reached. In production, such a procedure is most preferred. It has been found to be advantageous to continue stirring, after the pH has been set, at 40-80° C., preferably 50-75° C., with preference 60-70° C. The additional stirring period may be from 1 to 24 hours, preferably 2-10 hours, particularly preferably 2-4 hours. The organic solvent is then substantially distilled off, this may be carried out at atmospheric pressure or, in a more gentle manner, under reduced pressure. Once the organic solvent has been substantially distilled off, the mixture is allowed to cool to 15-25° C., e.g. using a ramp, and may then again be stirred for 1 to 64 hours (the 64 hours serve to demonstrate the robustness of the process, see Example 3b); however, the extra stirring time is preferably between 1 and 24 hours, and 1-5 hours are generally sufficient.

The isolation is carried out by methods known to the person skilled in the art, for example by filtration or using a centrifuge. The filter cake obtained in this manner can be washed once or several times with a solvent or solvent mixture. This is followed by drying under reduced pressure, preferably <100 mbar, at elevated temperature (50 to 80° C., preferably 50° C.). In some cases, the use of a carrier gas has been found to be advantageous.

It is also possible, prior to the distillative removal of the solvent, to re-adjust the pH to pH 5-7 using an organic acid, for example formic acid, citric acid, acetic acid, or an inorganic acid, for example hydrochloric acid, sulfuric acid, phosphoric acid, or an acidic salt, for example sodium dihydrogen phosphate, potassium bisulfate or sodium bisulfate, and then to carry on as described above.

Using the procedure described above, it is possible to prepare crude products of very high chemical purity. The enantiomeric excess of the crude products (I) and (Ia) is generally >97% e.e. The content of (IIIa) or (IIIb) has been reduced to below 0.15%, preferably below 0.1% and in particular below 0.05%.

It has been found to be advantageous to subject a crude product obtained in this manner of the formula (I) or (Ia) to an additional crystallization to improve both chemical and especially optical purity, since the enantiomeric excesses of the crude products are generally >97% e.e. To this end, a final crystallization process was developed: For reasons of GMP, the crude product (I) or (Ia) is dissolved in ethanol (if required with heating) and then subjected to particle filtration, preferably using spirits or ethanol denatured with toluene. In some cases, depending on the technical equipment, the crystallization can also be carried out under pressure, at elevated temperature (advantage: less solvent); however, recrystallization from aqueous ethanol solutions (under elevated pressure or at atmospheric pressure) is also possible. Under atmospheric pressure or reduced pressure, the mixture is then concentrated to about ⅓ to ⅙ of the original volume, preferably ¼ to ⅕; this results in the crystallization of the product. In some cases, for example when large volumes have to be distilled off over long periods of time, it has been found to be advantageous to carry out the distillative removal under reduced pressure, keeping the internal temperature low to avoid decomposition and byproduct formation. After the distillation has ended, the mixture is cooled to 0° C. and the crystals then isolated and dried at 40 to 50° C. under reduced pressure. The yields are generally >88% of theory. The chemical purity and the content achieved correspond to the criteria for commercial products according to ICH guidelines. In pilot plant batches, the residual solvent content, in the present case ethanol content, is generally <0.05%. The optical purity is >>99% e.e.

In a particularly preferred process, in particular for operation on an industrial scale, (+)-dibenzoyltartaric acid (III) is used; both the anhydrous form and the hydrate may be employed:

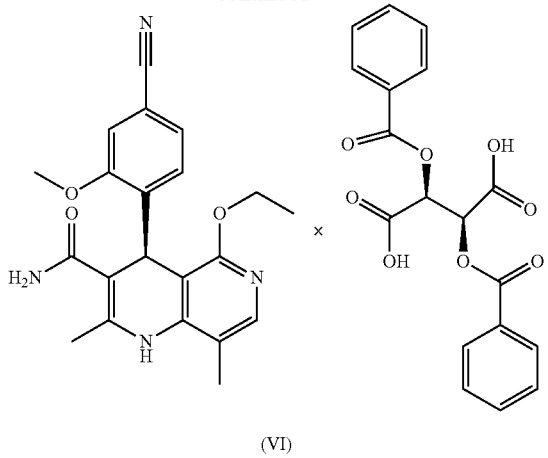

(VI)

The racemate resolution is preferably carried out in a spirits/water mixture. The subsequent release of crude finerenone

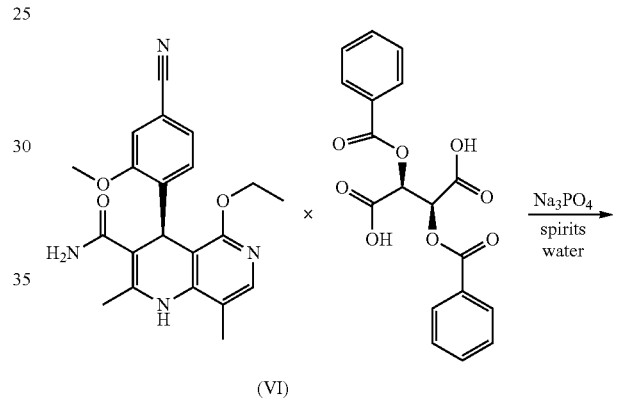

(VI)

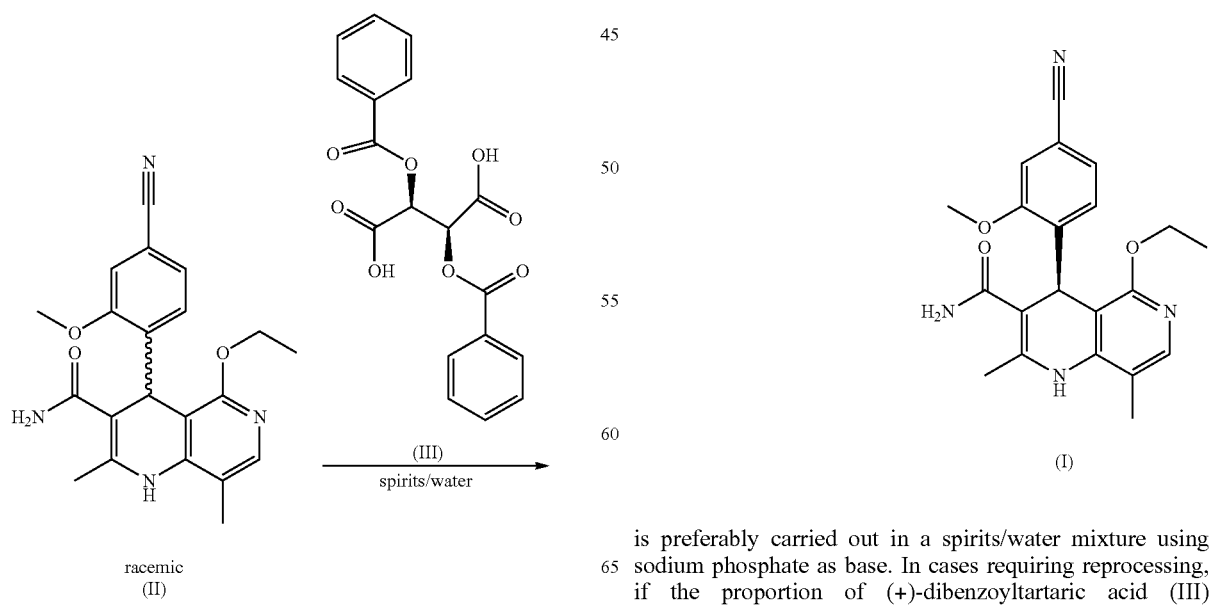

is preferably carried out in a spirits/water mixture using sodium phosphate as base. In cases requiring reprocessing, if the proportion of (+)-dibenzoyltartaric acid (III) is >0.15%,

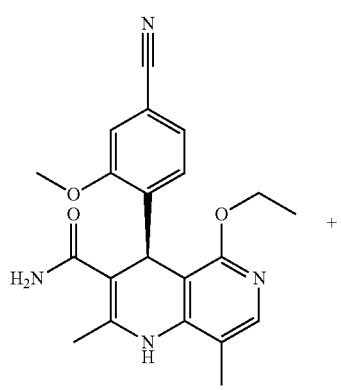

(I)

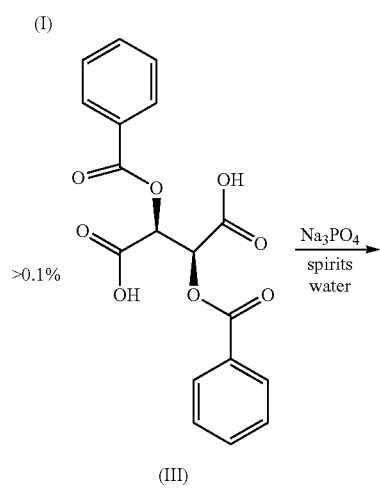

(III)

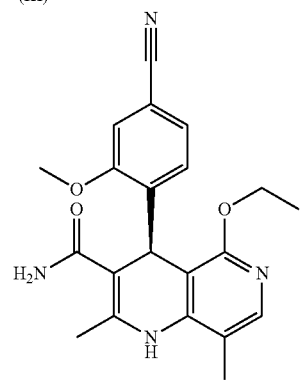

(I)

carbonate, lithium carbonate, ammonium bicarbonate, sodium bicarbonate, potassium bicarbonate, sodium phosphate, potassium phosphate, ammonium phosphate, preferably sodium hydroxide, sodium phosphate and potassium phosphate, particularly preferably sodium phosphate and potassium phosphate. The organic solvent, preferably ethanol, is then distilled off, either at atmospheric pressure or, more gently, under reduced pressure; this results in the precipitation of the corresponding other enantiomer. The product is filtered off, washed with water or water/solvent mixtures and dried. An appropriate final crystallization from spirits as described, for example, in Example 1e affords the compounds (I) and (Ia) in appropriate pure form.

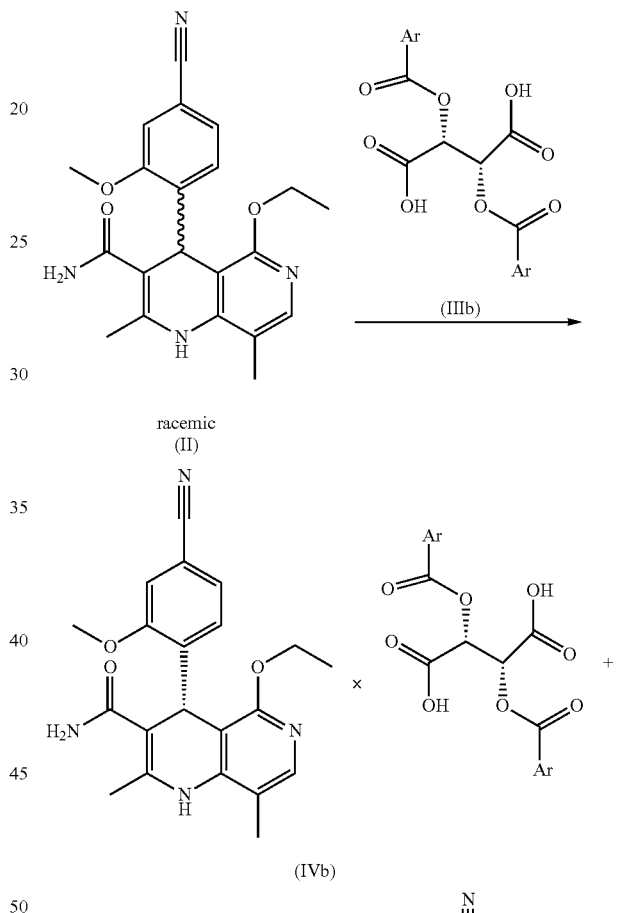

reprocessing is preferably carried out in a spirits/water mixture using sodium phosphate as base. Final crystallization to afford pure finerenone is preferably carried out using spirits as solvent. Here, a purity of 0.15%, preferably 0.1%, particularly preferably less than 0.05% impurities is achieved.

It is also possible to isolate the target enantiomer from the mother liquor. Here, initially, the appropriate diastereomeric salt (IVa), (IVb), (IVc) or (IVd) is prepared either from (I) or (Ia) and then isolated by filtration, and the mother liquor comprising the respective other diastereomer is then adjusted to a pH of pH>7, preferably pH 7.5, by addition of a base such as, for example, ammonia, aqueous sodium hydroxide solution, lithium hydroxide, potassium hydroxide, ammonium carbonate, sodium carbonate, potassium

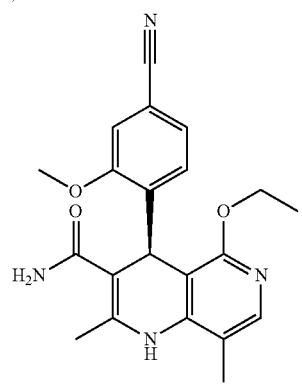

(I) mother liquor

Accordingly, the present application furthermore provides finerenone (I) having a dibenzoyltartaric acid content of ≤0.15%, obtained by reacting the racemate (II)

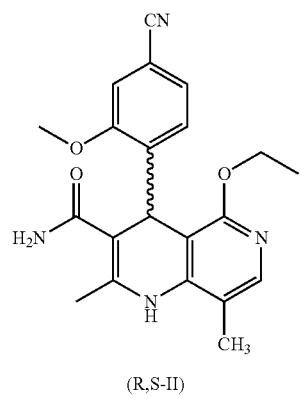

(R,S-II)

with dibenzoyltartaric acid of the formula (III)

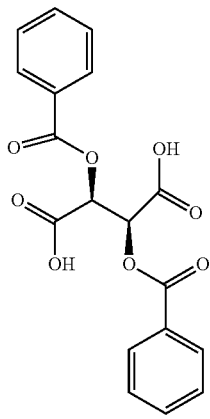

in a spirits/water mixture to give the diastereomeric salt (VI)

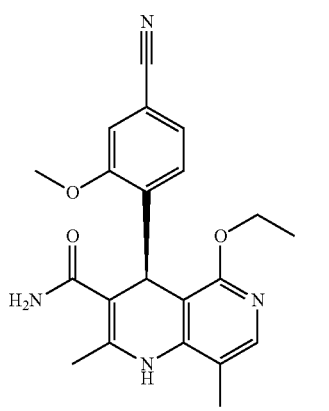

(VI)

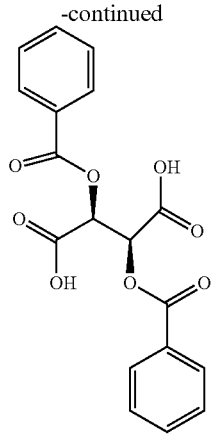

and subsequently releasing finerenone (I)

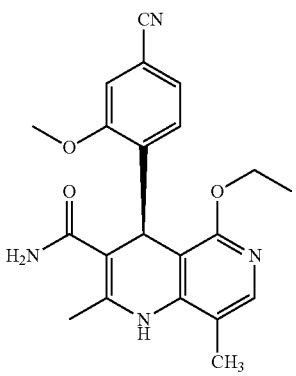

(I)

using sodium phosphate, also in a spirits/water mixture, and then again reacting with sodium phosphate in a spirits/water mixture and then crystallizing pure finerenone having a dibenzoyltartaric acid content of ≤0.15%; in a particularly preferred embodiment, finerenone having a dibenzoyltartaric acid content of ≤0.1%, in particular less than 0.05%, is obtained.

EXPERIMENTAL SECTION

Abbreviations and Acronyms

EtOH ethanol
DB tartaric acid dibenzoyltartaric acid
DMSO dimethyl sulfoxide
HPLC high-pressure, high-performance liquid chromatography
1H-NMR 1H nuclear magnetic resonance spectrometry
IT internal temperature
MS mass spectrometry
RT retention time
RRT relative retention time
TFA trifluoroacetic acid
TM mantle temperature
XRPD X-ray powder diffraction
spirits ethanol denatured with 2% toluene

EXAMPLES
Table 3 below shows the structures of the compounds recovered in HPLC. Assignment of the retention times in HPLC is shown below.
TABLE 3
finerenone (I)
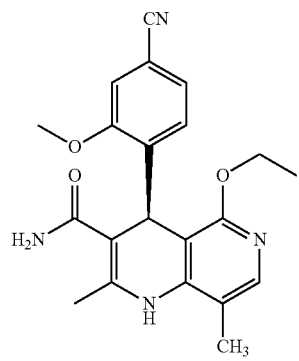 [SMILES: CCOc1ncc(C)c2c1[C@H](c1ccc(C#N)cc1OC)C(C(N)=O)=C(C)N2]
impurity A
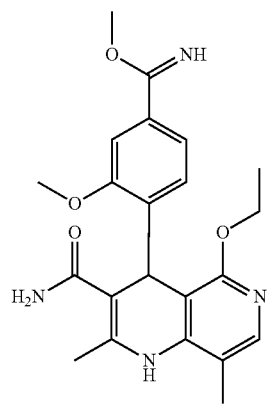 [SMILES: CCOc1ncc(C)c2c1C(c1ccc(C(=N)OC)cc1OC)C(C(N)=O)=C(C)N2]
impurity B
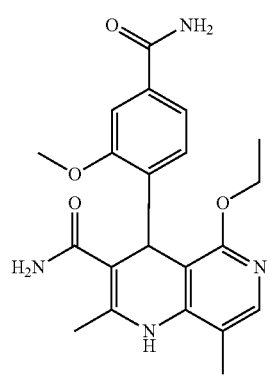 [SMILES: CCOc1ncc(C)c2c1C(c1ccc(C(N)=O)cc1OC)C(C(N)=O)=C(C)N2]
TABLE 3-continued
impurity C
(unknown structure, always significantly less than 0.1%)
impurity D
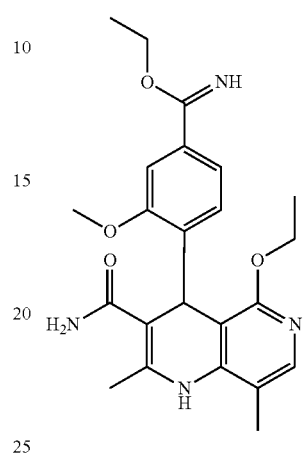
impurity E
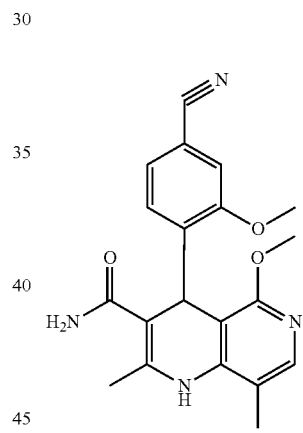
impurity F
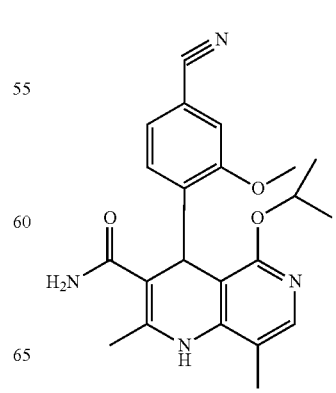

TABLE 3-continued
impurity G
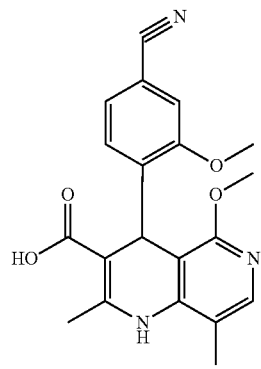 [SMILES: COc1cc(C#N)ccc1C1C(C(=O)O)=C(C)Nc2c(C)cnc(OC)c21]
impurity H
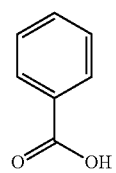
impurity I
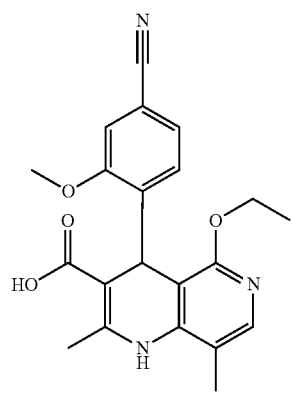 [SMILES: CCOc1ncc(C)c2c1C(c1ccc(C#N)cc1OC)C(C(=O)O)=C(C)N2]
impurity J
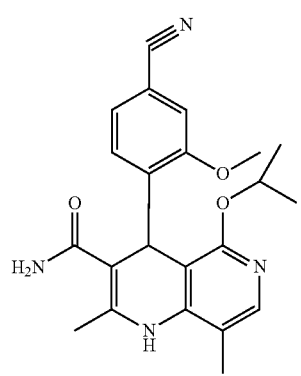 [SMILES: COc1cc(C#N)ccc1C1C(C(N)=O)=C(C)Nc2c(C)cnc(OC(C)C)c21]
TABLE 3-continued
impurity K
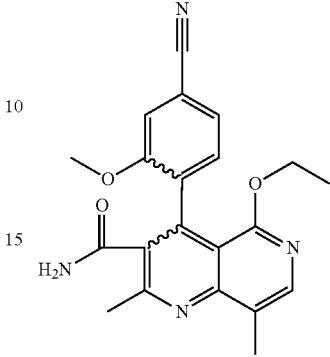
impurity N (III)
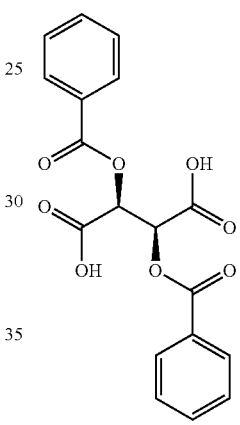
1) Analytical Method for Checking the Content of Impurities and the Enantiomeric Purity at the Stage of the Dibenzoyltartaric Acid
Content and Organic Impurities
|  | RT (min) | RRT |
| --- | --- | --- |
| dibenzoyltartaric acid | approx. 11.1 | 1.00 |
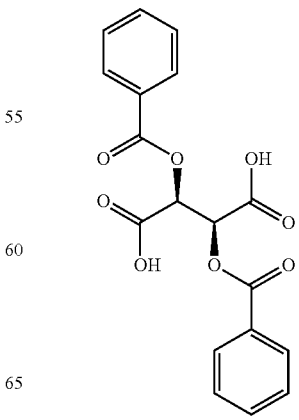

-continued

| | RT (min) | RRT |
|---|---|---|
| monobenzoyltartaric acid | Approx. 5.1 | 0.46 |
| benzoic acid | Approx. 7.6 | 0.69 |

Instrument: ultrahigh-performance liquid chromatograph (having a pressure range of up to 1200 bar with temperature-controlled column oven and UV detector)

Column: YMC Triart C8 length: 100 mm, internal diameter: 3.0 mm, particle size: 1.9 μm max pressure: 1000 bar Conditions: 20° C.; 0.50 ml/min; 1.7 μl (10° C.); 240 nm/6 nm Eluent: A: 0.1% TFA in water; B: acetonitrile Gradient: time (min) A (%) B (%)

| time (min) | A (%) | B (%) |
|---|---|---|
| 0.0 | 90.0 | 10.0 |
| 15.0 | 35.0 | 65.0 |
| 16.0 | 20.0 | 80.0 |
| 20.0 | 20.0 | 80.0 |

Enantiomeric Purity:

| | RT (min) | RRT |
|---|---|---|
| (+)-dibenzoyltartaric acid | 2.1 | 1.00 |
| (−)-dibenzoyltartaric acid | 3.9 | 1.86 |

Instrument: high-performance liquid chromatograph with temperature-controlled column oven and UV detector Column: Chiralpak IC length: 250 mm, internal diameter: 4.6 mm, particle size: 5.0 μm max pressure: 300 bar Conditions: 40° C.; 2.0 ml/min; 5 μl; 234 nm/6 nm Eluent: A: heptane; B: 0.1% TFA in ethanol isocratic: A(%) 80: B (%) 20

2) Analytical Method for Checking the Content of Impurities and the Enantiomeric Purity at the Stage of the Diastereomeric Salt Content and Organic Impurities

| | RT (min) | RRT |
|---|---|---|
| finerenone (I) | 6.2 | 1.00 |
| impurity A | 3.3 | 0.53 |
| impurity B | 3.7 | 0.60 |
| impurity C | 3.9 | 0.62 |
| impurity D | 4.4 | 0.70 |
| impurity E | 5.5 | 0.89 |
| impurity F | 6.8 | 1.10 |
| impurity G | 7.2 | 1.17 |
| impurity H | 7.7 | 1.25 |
| impurity I | 7.8 | 1.27 |
| impurity J | 8.4 | 1.36 |
| impurity K | 10.4 | 1.69 |
| impurity N | 11.1 | 1.80 |

Instrument: ultrahigh-performance liquid chromatograph (having a pressure range of up to 1200 bar with temperature-controlled column oven and UV detector)

Column: YMC Triart C8 length: 100 mm; internal diameter: 3.0 mm; particle size: 1.9 μm max pressure: 1000 bar Conditions: 20° C.; 0.50 ml/min; 3.5 μl (10° C.); 242 nm/6 nm Eluent: A: 0.1% TFA in water; B: acetonitrile Gradient:

| time (min) | A (%) | B (%) |
|---|---|---|
| 0.0 | 90.0 | 10.0 |
| 15.0 | 35.0 | 65.0 |
| 16.0 | 20.0 | 80.0 |
| 20.0 | 20.0 | 80.0 |

Enantiomeric Purity:

| | RT (min) | RRT |
|---|---|---|
| finerenone (I) | 5.34 | 1.00 |
| (Ia) | 6.14 | 1.15 |

Instrument: high-performance liquid chromatograph with temperature-controlled column oven and UV detector Column: Lux 3 μm i-Cellulose-5 length: 150 mm, internal diameter: 4.6 mm, particle size: 3.0 μm max pressure: 300 bar Conditions: 40° C.; 1.0 ml/min; 10 μl (20° C.); 252 nm/6 nm Eluent: A: 20 mmol ammonium acetate buffer pH 9.0 (1.54 g ammonium acetate in 1 l of Milli-Q water, adjusted to pH 9.0 with ammonia)

B: acetonitrile isocratic: A (%) 50: B (%) 50

3) Analytical Method for Checking the Content of Impurities and the Enantiomeric Purity at the Stage of Crude Finerenone (I).

Content and Organic Impurities

|  | RT (min) | RRT |
|---|---|---|
| finerenone (I) | 6.2 | 1.00 |
| impurity A | 3.3 | 0.53 |
| impurity B | 3.7 | 0.60 |
| impurity C | 3.9 | 0.62 |
| impurity D | 4.4 | 0.70 |
| impurity E | 5.5 | 0.89 |
| impurity F | 5.6 | 0.91 |
| impurity G | 6.8 | 1.10 |
| impurity H | 7.6 | 1.23 |
| impurity K | 10.4 | 1.68 |
| impurity N | 11.1 | 1.79 |

Instrument: ultrahigh-performance liquid chromatograph (having a pressure range of up to 1200 bar with temperature-controlled column oven and UV detector)
Column: YMC Triart C8
  length: 100 mm; internal diameter: 3.0 mm; particle size: 1.9 μm
  max pressure: 1000 bar
Conditions: 20° C.; 0.50 ml/min; 1.7 μl (10° C.); 252 nm/6 nm and 230 nm/6 nm for the evaluation of DB-tartaric acid
Eluent: A: 0.1% TFA in water; B: acetonitrile
Gradient:

| time (min) | A (%) | B (%) |
|---|---|---|
| 0.0 | 90.0 | 10.0 |
| 15.0 | 35.0 | 65.0 |
| 16.0 | 20.0 | 80.0 |
| 20.0 | 20.0 | 80.0 |

Enantiomeric Purity:

|  | RT (min) | RRT |
|---|---|---|
| finerenone (I) | about 11 | 1.00 |
| (Ia) | about 9 | 0.82 |

Method A
  Instrument: high-performance liquid chromatograph with temperature-controlled column oven and UV detector
  Column: Chiralpak IA
    length: 250 mm, internal diameter: 4.6 mm, particle size: 5.0 μm
    max pressure: 300 bar
  Conditions: 40° C.; 0.8 ml/min; 5 μl (20° C.); 255 nm/6 nm
  Eluent: A: acetonitrile; B: methyl tert-butyl ether (MTBE) isocratic: A (%) 90: B (%) 10
Enantiomeric Purity:

|  | RT (min) | RRT |
|---|---|---|
| finerenone (I) | 5.7 | 1.00 |
| enantiomer (Ia) | 6.8 | 1.19 |

Method B
  Instrument/detector: high-performance liquid chromatograph with temperature-controlled column oven, UV detector and data evaluation system.
  Measurement wavelength: 252 nm
  Oven temperature: 40° C.
  Column: Chiralpak IC
    length: 150 mm, internal diameter: 4.6 mm, particle size: 3 m
  Mobile phase: A: 50% buffer 20 mM ammonium acetate pH 9
    B: 50% acetonitrile
  Flow rate: 1 ml/min
  Elution time: 8 min
  Equilibration: not required, isocratic
  Sample solvent: mobile phase
  Test solution: about 0.5 mg/ml of the substance racemate, dissolved in sample solvent
  Comparative solution: A comparative solution analogous to the sample solution is prepared
  Injection volume: 10 μl The measured values stated in the examples below for enantiomer determination were all determined according to Method B. Some values, especially those of the batches prepared in the pilot plant, were, for comparison, measured again using Method A, and gave comparable results.

The HPLC analysis data given in the examples which follow with respect to purity and content of the end product pure finerenone (I) refer only to impurities present in the product in an amount of >0.05%. This is essentially impurity E. All other impurities shown in the Table listed above are generally <0.05%. The structure of such impurities was determined by isolation from enriched mother liquors.

Example 1

Laboratory batch using anhydrous (+)-O,O-dibenzoyl-D-tartaric acid (III)

Example 1a

Tartrate Salt (IV) Preparation 250 g (660.616 mmol) of finerenone (II) racemate were initially charged into 3500 ml of a mixture consisting of ethanol (denatured with toluene)/water=75:25 (v/v) at room temperature (about 23° C.). 130.2 g (363.339 mmol) of (+)-O,O-dibenzoyl-D-tartaric acid (III) were added using a funnel for solids, subsequently rinsing with 250 ml of a mixture consisting of ethanol (denatured with toluene)/water=75:25 (v/v). The resulting suspension was heated to an internal temperature of 75° C. over 0.75 hours and then stirred at this temperature for 3.0 hours. Subsequently, using a cooling ramp, the mixture was cooled to 23° C. over 5.0 hours and then stirred at this temperature overnight (about 16 hours). The suspension was filtered off through a frit, rinsing once with 250 ml of a mixture consisting of ethanol (denatured with toluene)/water=75:25 (v/v). Wet yield: 334.7 g. The wet product was then dried overnight (about 16 hours) at 50° C. under reduced pressure (<100 mbar). Yield: 250.2 g (100.08% of theory) of a colourless crystalline powder.

Analytical Results:

| Finerenone (I) | 47.2% by weight (HPLC) |
|---|---|
| Enantiomeric excess | 97.68% e.e. |
| Largest unknown secondary component at RT 5.606 min. | 0.47% |
| Residual solvents: |  |
| EtOH | 2.24% |
| toluene | 0.0% |

MS (EIpos): m/z=379 [M+H]$^+$
$^1$H-NMR (400 MHz, DMSO-d$_6$): δ=1.05 (t, 3H), 2.12 (s, 3H), 2.18 (s, 3H), 3.82 (s, 3H), 3.99-4.07 (m, 2H), 5.39 (s, 1H), 5.89 (s, 2H), 6.60-6.84 (m (broad signal), 2H), 7.14 (d, 1H), 7.28 (dd, 1H), 7.37 (d, 1H), 7.55 (s, 1H), 7.61 (t, 4H), 7.69 (s, 1H), 7.75 (t, 2H), 8.04 (d, 4H), 12.50-15.40 (very broad signal, 2H) and signal of the solvent DMSO and increased water signal: δ=2.5-2.6, as well as smaller peaks at δ=3.40-3.50 (q) and δ=1.05-1.10 (t), superimposed signals from residual solvent ethanol.

The colourless crystalline powder (finerenone-(+)-O,O-dibenzoyl-D-tartaric acid complex (VI)) obtained according to Example 1a was examined by XRPD under the following conditions at 25° C.:

Sample preparation: The powder is prepared as a thin layer between two films (e.g. polyacetate)
  Apparatus: X-ray powder diffractometer X'Pert Pro
  Generator: 40 kV/40 mA
  Detector: PIXcel
  Radiation: CuKa radiation
  Wavelength: 1.5406 Å
  Technique: transmission
  Scanning range: 2° £ 2Q £ 40°
  Stepwidth: 0.013° 2Q
  Measuring time: 25 s/step
The results are shown in FIG. 1 and Table 1.

TABLE 1

| No. | Position | No. | Position | No. | Position | No. | Position |
|---|---|---|---|---|---|---|---|
| 1 | 7.1576 | 18 | 18.3972 | 35 | 25.6188 | 52 | 31.8820 |
| 2 | 8.3525 | 19 | 18.8961 | 36 | 25.7895 | 53 | 32.2890 |
| 3 | 8.6020 | 20 | 19.2638 | 37 | 25.9996 | 54 | 32.6173 |
| 4 | 11.2018 | 21 | 20.3404 | 38 | 26.3410 | 55 | 32.9586 |
| 5 | 11.7664 | 22 | 20.6556 | 39 | 27.0106 | 56 | 34.5343 |
| 6 | 12.5279 | 23 | 20.9182 | 40 | 27.8510 | 57 | 35.7291 |
| 7 | 13.6703 | 24 | 21.6141 | 41 | 28.0873 | 58 | 36.6614 |
| 8 | 13.9066 | 25 | 22.0474 | 42 | 28.3237 | 59 | 37.7381 |
| 9 | 14.3399 | 26 | 22.2049 | 43 | 28.5863 | 60 | 38.1976 |
| 10 | 14.5631 | 27 | 22.5332 | 44 | 28.8620 | 61 | 38.7228 |
| 11 | 14.7863 | 28 | 22.8221 | 45 | 29.2034 | 62 | 39.6026 |
| 12 | 14.9702 | 29 | 23.2554 | 46 | 29.4003 | | |
| 13 | 16.1650 | 30 | 23.6361 | 47 | 29.7942 | | |
| 14 | 16.3488 | 31 | 24.0300 | 48 | 30.0306 | | |
| 15 | 16.7427 | 32 | 24.5947 | 49 | 30.1356 | | |
| 16 | 17.2548 | 33 | 24.8179 | 50 | 30.5164 | | |
| 17 | 17.4912 | 34 | 25.2118 | 51 | 30.9497 | | |

Example 1b

Preparation Crude Product (I)

At room temperature, 248 g of the compound (IV) prepared in Example 1a were suspended in 2480 ml of a mixture consisting of ethanol (denatured with toluene)/water=20:80 (v/v) (the pH was determined to be pH=4). Subsequently, 819.6 g of an aqueous sodium phosphate solution (100 g of sodium phosphate dissolved in 1000 ml of water) were added dropwise over 60 minutes and the pH was adjusted to pH=7.2. The mixture was stirred at 23° C. for a further 50 minutes (pH=7.1). Subsequently, 98.3 g of an aqueous sodium phosphate solution (100 g of sodium phosphate dissolved in 1000 ml of water) were added dropwise over 10 minutes and the pH was adjusted to pH=7.5. Over one hour, the mixture was heated to an internal temperature of 50° C. and stirred at this temperature for 3.0 hours. The mixture was cooled to 22° C. over one hour and stirred at this temperature for another hour. The crystals are filtered off through a frit and washed once with 200 ml and once with 100 ml of a mixture consisting of ethanol (denatured with toluene)/water=20:80 (v/v) and twice with 200 g of water. Wet yield: 263.4 g. The wet product was then dried over the weekend (>48 hours) at 50° C. under reduced pressure (<100 mbar). Yield: 116.9 g (93.52% of theory) of a colourless crystalline powder.

Analytical Results:

| Finerenone (I) | Purity: 99.86 area % (HPLC); Content: 100.0% by weight |
|---|---|
| enantiomeric excess | 97.02% e.e. |
| Largest secondary component impurity E | 0.07% |
| Residual solvents: | |
| EtOH | 0.19% |
| toluene | 0.13% |
| Water (Karl-Fischer) | 0.042% |

MS (EIpos): m/z=379 [M+H]$^+$ $^1$H-NMR (400 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m (broad signal), 2H), 7.14 (d, 1H), 7.28 (dd, 1H), 7.37 (d, 1H), 7.55 (s, 1H), 7.69 (s, 1H) and signal of the solvent DMSO and significantly increased water signal: δ=2.5-2.6, and also very small peak at δ=3.38 (not assigned)

Example 1c

Preparation Pure Product (I)

116.0 g of the crude product (I) prepared in Example 1b were suspended in 2330 ml of ethanol (denatured with toluene) and then heated to reflux. On heating, the product went into solution. Stirring was continued at this temperature for one hour. The solution was filtered off through a heated pressure filter (T=75° C.) and the pressure filter was then rinsed with 30 ml of ethanol (denatured with toluene). The solvent was then distilled off to the point where a final volume of about 4-fold (with respect to the substance employed: 116 g×4~484 ml) had been achieved (about 1920 ml were distilled off). The mixture was then cooled to an internal temperature of 23° C. (duration about 1.5 to 2 hours). The mixture was then stirred at an internal temperature of 3° C. for 2 hours. The product was filtered off and rinsed once with 100 ml of ethanol (denatured with toluene). Wet yield: 124 g. The wet product was dried at 50° C. over the weekend (>48 h) under reduced pressure (<100 mbar). Yield: 112.6 g (97.07% of theory) of a colourless crystalline powder, fine needle-like crystals.

Analytical Results:

| Finerenone (I) | Purity: 99.86 area % (HPLC); Content: 99.5% by weight |
|---|---|
| enantiomeric excess | 100% e.e. |
| Largest secondary component impurity E | 0.07% |
| Residual solvents: | |
| EtOH | 0.05% |
| toluene | 0.00% |
| Water (Karl-Fischer) | 0.00% |

MS (EIpos): m/z=379 [M+H]$^+$ $^1$H-NMR (400 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m (broad signal), 2H), 7.14 (d, 1H), 7.28 (dd, 1H), 7.37 (d, 1H), 7.55 (s, 1H), 7.69 (s, 1H) and small signals of solvents DMSO and Wasser at δ=2.5-2.6 and a very small peak at δ=3.38 (not assigned)

Modification: Mod A (according to the definition in WO2016/016287 A1 where the absolute configuration was determined by X-ray)

Example 2

Laboratory batch using (+)-O,O-dibenzoyl-D-tartaric acid hydrate (III)

Example 2a

Tartrate Preparation 350.0 g racemate (II) were initially charged at room temperature and 3112 g of spirits were then added. 1200 g of water were then added. 191.4 g of (+)-O,O-dibenzoyl-D-tartaric acid monohydrate (III) were added using a funnel for solids, subsequently rinsing with 113 g of water. The suspension was heated to an internal temperature of 75° C. over one hour and then stirred at 75° C. for 3 hours. Subsequently, using a cooling ramp, the mixture was cooled to 23° C. over 5.0 hours and then stirred at this temperature overnight (about 18 hours). The suspension was filtered off through a frit and washed twice with a mixture consisting of 332.3 g of spirits and 140.2 g of water. Wet yield: 487.6 g. The wet product was then dried over the weekend (>48 hours) at 50° C. under reduced pressure (<100 mbar). Yield: 351.0 g (100.29% of theory) of a colourless crystalline powder.

| Finerenone (I) | Content: 47.92% by weight |
| --- | --- |
| enantiomeric excess | 97.84% e.e. |
| Largest secondary component at RT 5.86 min | 0.22% |
| Residual solvents: | |
| EtOH | 2.594% |
| toluene | 0.003% |

In a manner analogous to that described in Examples 1b and 1c, pure finerenone (I) can be prepared from this tartrate salt.

Example 3

Preparation of 3 batches of pure finerenone (I) in a pilot plant, starting with 2 kg of racemate (II).

Example 3a

Tartrate Preparation (IV)

2.00 kg (5.285 mol) of racemic finerenone (IL) were initially charged into 28.0 l of a mixture consisting of ethanol (denatured with toluene)/water=75:25 (v/v) at room temperature (about 23° C.). 1.042 kg (2.907 mol) of (+)-O,O-dibenzoyl-D-tartaric acid (III) were added using a funnel for solids, subsequently rinsing with 2 l of a mixture consisting of ethanol (denatured with toluene)/water=75:25 (v/v). The resulting suspension was heated to an internal temperature of 75° C. over 45 minutes and then stirred at this temperature for 3.0 hours. Subsequently, using a cooling ramp, the mixture was cooled to 23° C. over 5.0 hours and then stirred at this temperature overnight (about 16 hours). The suspension was filtered off via a frit, rinsing once with 2 l of a mixture consisting of ethanol (denatured with toluene)/water=75:25 (v/v) and sucked dry for 10 minutes. Wet yield: 2.69 kg. The wet product was then dried at 50° C. under reduced pressure (<100 mbar) until the mass remained constant (after about 17 hours). Yield: 2.009 kg (~100% of theory) of a colourless crystalline powder.

Example 3b

Preparation Crude Product (I)

At room temperature (about 23° C.), 2.006 kg of the compound (IV) prepared in Example 3a were suspended in 20.0 l of a mixture consisting of ethanol (denatured with toluene)/water=1:4 (v/v) (the pH was determined to be pH=4). 6.05 kg of a 9.09% strength aqueous sodium phosphate solution was then added dropwise and the pH was adjusted to pH=7.2. The mixture was stirred at 23° C. for approx. a further 50 minutes (pH=7.17). 0.65 kg of a 9.09% strength aqueous sodium phosphate solution was then added dropwise and the pH was adjusted to pH=7.5. Over one hour, the mixture was heated to an internal temperature of 50° C. and stirred at this temperature for 3.0 hours. The mixture was cooled to 22° C. over one hour and stirred at this temperature over the weekend (about 64 hours*). The crystals are filtered off through a K800 Seitz filter plate and washed once with 1.6 l and once with 0.8 l of a mixture consisting of ethanol (denatured with toluene)/water=20:80 (v/v) and twice with in each case 1.6 l of water. Wet yield: 1.82 kg. The wet product was then dried at 50° C. under reduced pressure (<100 mbar) until the mass remained constant (after about 17 hours). Yield: 0.978 kg (97.8% of theory) of a colourless crystalline powder.

*) for technical reasons, the mixture was stirred over the weekend; usually, 14 hours of stirring are sufficient.

Example 3c

Preparation Pure Product (I)

250 g of the crude product (I) prepared in Example 3b were suspended in 5000 ml of ethanol (denatured with toluene) and then heated to reflux. On heating, the product went into solution. Stirring was continued at this temperature for one hour. The solution was filtered off through a heated pressure filter (T=85° C.) and the pressure filter was then rinsed with 200 ml of ethanol (denatured with toluene). The solvent was then distilled off to the point where a final volume of about 4-fold (with respect to the substance employed: 250 g×4~1000 ml) had been achieved (about 4200 ml were distilled off). The mixture was then cooled to an internal temperature of 4-5° C. (ramp: duration about 4 hours). The mixture was then stirred at an internal temperature of 4-5° C. for one hour. The product was filtered off and rinsed once with 220 ml of ethanol (denatured with toluene). Wet yield: 251.2 g. The wet product was dried at 50° C. over the weekend (>48 h) under reduced pressure (<100 mbar). Yield: 223.0 g (89.2% of theory) of a colourless crystalline powder.

The results of 3 batches starting in each case with 2 kg of the racemate of finerenone (II) are summarized in Table 4 below:

TABLE 4

Tartrate salt (IV)

| Batch | Racemate (II) employed kg | Yield: kg | Yield: % of theory |
|---|---|---|---|
| Batch 1 (Example 3a) | 2 | 2.009 | ~100 |
| Batch 2 | 2 | 2.025 | ~100 |
| Batch 3 | 2 | 2.027 | ~100 |

| Batch | Content (I) % by weight | Purity (HPLC) | Enantiomeric excess e.e. % | Residual solvents: |
|---|---|---|---|---|
| Batch 1 (Example 3a) | 49.20 | Largest secondary compound at RT 5.606 min: 0.22% | 97.69 | ethanol: 2.55% toluene: 0.01% |
| Batch 2 | 49.80 | Largest secondary compound at RT 5.606 min: 0.11% | 97.49 | ethanol: 2.74% toluene: 0.00% |
| Batch 3 | 50.06 | Largest secondary compound at RT 5.606 min: 0.14% | 97.64 | ethanol: 2.58% toluene: 0.004% |

Crude Product (I)

| Batch | Tartrate salt (IV) employed: kg | Yield: kg | Yield: % of theory |
|---|---|---|---|
| Batch 1 (Example 3b) | 2.009 | 0.978 | 97.8 |
| Batch 2 | 2.025 | 0.985 | 98.5 |
| Batch 3 | 2.027 | 0.987 | 98.7 |

| Batch | Content (I) % by weight | Purity (HPLC) | Enantiomeric excess e.e. % | Residual solvents: |
|---|---|---|---|---|
| Batch 1 (Example 3a) | 98.10 | finerenone (I): 99.85% Largest secondary compound impurity E: 0.07% | 98.15 | ethanol: 0.203% toluene: 0.117% |
| Batch 2 | 99.00 | finerenone (I): 99.83% Largest secondary compound impurity E: 0.08% | 97.93 | ethanol: 0.110% toluene: 0.073% |
| Batch 3 | 99.70 | finerenone (I): 99.84% Largest secondary compound impurity E: 0.07% | 97.97 | ethanol: 0.118% toluene: 0.076% |

In all 3 batches, the (+)-O,O-dibenzyoyl-D-tartaric acid content was: 0.00%

Pure product (I)

| Batch | Crude product (I) g | Yield: g | Yield: % of theory |
|---|---|---|---|
| Batch 1 (Example 3c) | 250 | 223 | 89.2 |
| Batch 2 | 250 | 235 | 94.0 |
| Batch 3 | 250 | 226 | 91.8 |

| Batch | Content (I) % by weight | Purity (HPLC) | Enantiomeric excess e.e. % | Residual solvents: |
|---|---|---|---|---|
| Batch 1 (Example 3a) | 99.40 | finerenone (I): 99.82% impurity E 0.08% | 100.00 | ethanol: 0.074% toluene: 0 000% |
| Batch 2 | 99.80 | finerenone (I): 99.94% impurity E 0.08% | 100.00 | ethanol: 0.037% toluene: 0.000% |
| Batch 3 | 99.50 | finerenone (I): 99.85% impurity E 0.08% | 99.92 | ethanol: 0.033% toluene: 0.000% |

In all 3 batches, the (+)-O,O-dibenzyoyl-D-tartaric acid content (III) was 0.00%

Example 4

Industrial realization of the process. The examples which follow describe the realization of the process on an industrial scale. The results, such as yield and analytic data, of 2 batches of pure finerenone (I) are then represented in tables:

Example 4a

Tartrate Salt (IV) Preparation
The batch size was 80 kg of racemic finerenone (II).
In a 1600 l stirred vessel, 711.0 kg of spirits were initially charged at an IT of 20° C., following by addition of 300 kg of water, then 80.0 kg of racemate (II) and finally 41.7 kg of (+)-dibenzoyltartaric acid (III).
The mixture was heated to an IT of 75° C. and stirred for 3 h.
The mixture was cooled to an IT of 23° C. over 5 h (ramp) and stirred for another 16 h.
For centrifugation, the suspension was transferred into the inverting centrifuge, centrifuged, rinsed with a mixture consisting of 10.7 kg of spirits and 4.5 kg of water, then tumble-dried and removed.
Drying was carried out in a 300 l spherical drier at a mantle temperature of 50° C. and at 30 mbar. Drying was terminated at an internal temperature of 45° C. (duration about 6 h).
The product was cooled to 15° C. and then removed.

Example 4b

Crude Product (I)
The batch size was 89.3 kg of tartrate salt (IV) starting material
Preparation of a sodium phosphate solution
In a 630 l stirred vessel, 360.0 kg of fully demineralized water were initially charged at 20° C.
36.0 kg of sodium phosphate were added and dissolved
In a 1600 l stirred vessel, 141.1 kg of spirits were initially charged at 20° C.
714.2 kg of water and 89.3 kg of tartrate salt (IV) were then added
The mixture was heated to an internal temperature of 50° C.
295.1 kg of a sodium phosphate solution were then metered in
After 1.5 h, the pH was adjusted to pH=7.5 (+/−0.1) by addition of 35.4 kg of sodium phosphate solution
The mixture was left to stir and cooled via a ramp (3 h) to IT=22° C.
Stirring was then continued at IT=22° C. (18 h)
In a receiver, a mixture of 129.6 kg of water and 25.6 kg of spirits was prepared (for washing)
The suspension was metered into the inverting centrifuge (about 4 batches+residual batch) and, a little at a time, washed once with the mixture of 129.6 kg of water and 25.6 kg of spirits and once with 288.0 kg of fully demineralized water.
The product was removed and dried in a spherical drier (TM=50° C., 30 mbar, terminated at IT=45° C., about 6 h)
The product was cooled and removed at <30° C.

Example 4c

Reprocessing of the Crude Product (I)
In some cases, if the specification limit for (+)-dibenzoyltartaric acid (III) in the crude product is >0.1%, it has been found to be advantageous to carry out reprocessing (see Example 6) to ensure that the limit<0.1% is reproducibly achieved. In addition, the reprocessing process is virtually loss-free and generally affords the crude product in a yield of >95%.

Reprocessed Crude Product (I)
The batch size was 30 kg of crude product (I).
Preparation of a sodium phosphate solution: At room temperature, 2.3 kg of sodium phosphate were dissolved in 147.8 kg of water in a 250 l stirred receiver
At 20° C., 198.8 kg of spirits were initially charged in a 630 l stirred vessel and 120 kg of water were added, followed by the addition of 30 kg of crude product (containing (+)-dibenzoyltartaric acid (III) as stated in Table 5).
The mixture was heated to an internal temperature of 70° C. and stirred for 30 minutes.
At 70° C., 14.1 kg of the sodium phosphate solution prepared above were metered in, adjusting the pH to pH 8.9 (+/−0.1), and the mixture was stirred at 70° C. for 20 hours.
Using a ramp, the mixture was cooled to 44° C. over 60 minutes and 300 g of pure finerenone (I) seed crystals were added
The solvent was then distilled off at 200 mbar and an internal temperature of at most 60° C. and at the same time 369 kg of water were metered into the stirred vessel.
Finally, the mixture was cooled to 22° C. over 1.5 hours and the product was isolated on a pressurized suction filter and, in 3 portions, washed with a total of 180 l of water
At a mantle temperature of 50° C. and under reduced pressure (30 mbar), the product was then dried to weight constancy.
The product was allowed to cool to 15° C. and then removed.

Example 4d

Pure Product (I)
The batch size was 26 kg (2 times 13 kg) of reprocessed crude product (I)
In a 250 l stirred vessel, 13 kg of reprocessed crude product (I) were initially charged in 184.9 kg of spirits at 20° C., with the stirred vessel having been inertized beforehand
The solution was heated to a mantle temperature of 80° C. and stirred at 78° C. for 30 minutes (with dissolution of the product).
The solution was filtered through a 0.65 μm filter element (PP element Sartorius) (GMP filtration) and the filtrate was transferred into a 630 l stirred vessel.
The product was washed with 18.5 kg of spirits
This was repeated in 2 subdivided portions (2 times 13 kg of product) and the solutions were combined
The solvent was distilled off at atmospheric pressure to a final filling level of about 130 l (in two portions, mantle temperature: 104° C., duration about 6 hours)
The solution was cooled to 0° C. over 4 hours using a linear temperature ramp and then stirred for another hour.
The product suspension was isolated on a pressurized suction filter and washed with 45.9 kg of spirits
The wet product was then dried under reduced pressure (30 mbar) at 50° C. to weight constancy (about 12 h).
The mixture was cooled to 15° C. and the product was removed.

A summary of yield and analytical results of 3 industrial batches for the preparation of pure finerenone (I) is given in Table 5

Tartrate Salt (IV)

TABLE 5

| Batch | Racemate (II) employed kg | Yield tartrate salt (IV): kg | Yield: % of theory (not corrected for content) |
|---|---|---|---|
| Batch 1 (Example 4a) | 80 | 77.3 | 100 |
| Batch 2 | 80 | 81.2 | 105 |
| Batch 3 | 80 | 80.2 | 103 |

| Batch | Content tartrate salt (IV) % by weight | Content of finerenone (I) % by weight | Purity (HPLC) | Enantiomeric excess e.e. % |
|---|---|---|---|---|
| Batch 1 (Example 4a) | 94.2 | 48.4 | (+)-dibenzoyltartaric acid: 44.98% | 98.6 |
| Batch 2 | 95.4 | 49.0 | (+)-dibenzoyltartaric acid: 44.98% | 98.6 |
| Batch 3 | 94.2 | 48.4 | (+)-dibenzoyltartaric acid: 44.98% | 98.6 |

| | Crude Product (I) | | |
|---|---|---|---|
| Batch | Tartrate salt (IV) employed: kg | Yield (I, crude): kg | Yield: % of theory |
| Batch 1 (Example 4b) | 89.3 | 36.6 | 80 |
| Batch 2 | 89.3 | 44.2 | 96 |
| Batch 3 | 89.3 | 45.7 | 99 |

| Batch | Content (I) % by weight | Purity (HPLC) | Enantiomeric excess e.e. % | Residual solvents: |
|---|---|---|---|---|
| Batch 1 (Example 4b) | 98.5 | finerenone (I): 99.71% impurity E: 0.08% Sum of all organic secondary components: 0.29% (+)-dibenzoyltartaric acid: 0.71% | 98.8 | ethanol: 0.098% toluene: 0.048% |
| Batch 2 | 98.2 | finerenone (I): 97.70% impurity E: 0.08% Sum of all organic secondary components: 0.30% (+)-dibenzoyltartaric acid: 0.39% | 98.9 | ethanol: 0.151% toluene: 0.088% |
| Batch 3 | 100 | finerenone (I): 99.76% impurity E: 0.07% Sum of all organic secondary components: 0. 0.24% (+)-dibenzoyltartaric acid: 0.46% | 98.7 | ethanol: 0.102% toluene: 0.066% |

| | Crude product (I) after reprocessing | | |
|---|---|---|---|
| Batch | Input (I): kg | Yield (I): kg | Yield: % of theory |
| Batch 1 (Example 4c) | 30 | 29.8 | 99.33 |
| Batch 2 | 30 | 29.8 | 99.33 |

| Batch | Content (I) % by weight | Purity (HPLC) | Enantiomeric excess e.e. % | Residual solvents: |
|---|---|---|---|---|
| Batch 1 (Example 4c) | 99.6 | finerenone (I): 99.70% (+)-dibenzoyltartaric acid: <0.05% | 98.8 | ethanol: n.d. toluene: n.d. |

-continued

| | | Crude product (I) after reprocessing | | |
|---|---|---|---|---|
| Batch 2 | 99.6 | Largest secondary component impurity E: 0.08%<br>Sum of all organic secondary components: 0.3%<br>finerenone (I): 99.70%<br>(+)-dibenzoyltartaric acid: <0.05%<br>Largest secondary component impurity E: 0.08%<br>Sum of all organic secondary components: 0.3% | 98.8 | ethanol: n.d.<br>toluene: n.d. |

Pure Product, Pure Finerenone (I)

| | Pure produt, pure finerenone (I) | | |
|---|---|---|---|
| Batch | Input kg | Yield: kg | Yield: % of theory |
| Batch 1 (Example 4d) | 26 | 23.1 | 88.85 |
| Batch 2 | 26 | 22.9 | 88.08 |

| Batch | Content (I) % by weight | Purity (HPLC) | Enantiomeric excess e.e. % | Residual solvents: |
|---|---|---|---|---|
| Batch 1 (Example 4d) | 100 | finerenone (I): 99.8%<br>Sum of all organic secondary components: 0.2%<br>Largest secondary component impurity E: 0.08%<br>(+)-dibenzoyltartaric acid: <0.05 | 100 | ethanol: 0.044<br>toluene: 0.00<br>water: <0.2 |
| Batch 2 | 100 | finerenone (I): 99.8%<br>Sum of all organic secondary components: 0.2%<br>Largest secondary component impurity E: 0.08%<br>(+)-dibenzoyltartaric acid: <0.05% | 100 | ethanol: 0.063<br>toluene: 0.00<br>water: <0.2 |

Example 5

Several variants analogously to the procedure of Example 1b are suitable for releasing crude finerenone (I). Here, it was the objective to keep the proportion of (+)-O,O-dibenzoyl-D-tartaric acid (III) in the crude product as small as possible (0.15% or less). Specifically, final pH after the metered addition of the sodium phosphate solution, temperature, time of the metered addition of the sodium phosphate solution and additional stirring time were varied and the effect on the content of (+)-O,O-dibenzoyl-D-tartaric acid in the crude product was investigated.

Batch size: 100 g of tartrate salt (IV) in 158.0 g of spirits and 799.8 g of water Analytical data for the tartrate salt (IV) employed:

| Finerenone (I) | 48.05% by weight (HPLC) |
|---|---|
| enantiomeric excess | 97.71% e.e. |
| Largest unknown secondary component at Rt 5.606 min. | 0.28% |
| Residual solvents: | |
| EtOH | 2.576% |
| toluene | 0.006% |

The results are summarized in Table 6 below:

TABLE 6

| Batch | pH | Amount of Na$_3$PO$_4$ sol. (g) (100 g/l of water) | T (° C.) | Time of metered addition (min.) | Additional stirring time (min.) | Purity of finerenone (I) HPLC (%) | Yield (% of theory) | Proportion of (+)-dibenzoyltartaric acid (% by weight) |
|---|---|---|---|---|---|---|---|---|
| 1 | 7.5 | 400 | 50 | 30 | 180 | 99.17 | 97.2 | 0.0996 |
| 2 | 7.5 | 400 | 60 | 30 | 180 | 99.74 | 97.2 | 0.1101 |
| 3 | 8.0 | 444.9 | 50 | 30 | 180 | 99.86 | 97.0 | 0.0986 |
| 4 | 8.5 | 467.7 | 50 | 30 | 180 | 99.73 | 96.6 | 0.1298 |
| 5 | 9.0 | 480.3 | 50 | 30 | 180 | 99.85 | 97.4 | 0.1027 |
| 6 | 7.5 | 400 | 50 | 30 | 60 | 99.86 | 96.8 | 0.1010 |
| 7 | 7.5 | 400 | 50 | 30 | 300 | 99.87 | 97.2 | 0.1058 |
| 8 | 7.5 | 400 | 50 | 8 | 180 | 99.73 | 97.6 | 0.1294 |

Example 6

Reprocessing Process

Example 6a

Reprocessed Crude Product Reduction of the Proportion of (+)-O O-dibenzoyl-D-tartaric Acid<0.1%

This experiment served to demonstrate the robustness of the reprocessing process by intentionally employing a batch having an elevated proportion of (+)-O,O-dibenzoyl-D-tartaric acid (III).

A crude product which, according to analysis, still contained 0.77% (+)-O,O-dibenzoyl-D-tartaric acid (III) was used for reprocessing

| Crude finerenone (I) | Purity: 99.67 area % (HPLC); Content: 98.69% by weight |
|---|---|
| (+)-O,O-Dibenzoyl-D-tartaric acid | 0.77% |
| Largest secondary component impurity E | 0.07% |

Reprocessing of the Crude Product: Reduction of the Proportion of (+)-O,O-dibenzoyl-D-tartaric Acid (III)<0.1%

A crude product which, according to analysis, still contains 0.77% of (+)-O,O-dibenzoyl-D-tartaric acid (III) was used for reprocessing. The following procedure was adopted:

150 g of crude product (I) (containing 0.77% of (+)-O, O-dibenzoyl-D-tartaric acid (III)) were added into 600 g of water and 953.9 g of spirits and heated to 70° C. Over a period of one hour, the entire solid went into solution. The mixture was then stirred at 70° C. for 30 minutes. The pH is pH=5.0. By addition of 44.6 g of an aqueous sodium phosphate solution (15 g of sodium phosphate per 985 g of water), the pH was adjusted to pH=8.5 and the mixture was then stirred at 70° C. for 2 hours. Over a period of 30 minutes, the mixture was cooled to 53° C. and seeded with pure material (seed crystals). Stirring was then continued at 50-52° C. for 30 minutes. At 200 to 155 mbar and an internal temperature, the ethanol was distilled off virtually completely, and at the same time 1845 ml of water were metered in (the filling level was kept constant: amount distilled off=amount of water added). Heating was switched off and the suspension was stirred at 23° C. overnight. The crystals were filtered off via a frit and washed three times with 300 ml of water in each case. Wet yield: 218.9 g. The wet product was dried at 50° C. over the weekend (>48 hours) under reduced pressure (<100 mbar). Yield: 146.7 g (97.8% of theory)

| Finerenone (I) | Purity: 99.87 area % (HPLC); Content: 100.3% by weight |
|---|---|
| enantiomeric excess | 97.87% e.e. |
| (+)-O,O-Dibenzoyl-D-tartaric acid | 0.00% |
| Largest secondary component impurity E | 0.07% |
| Residual solvents: | |
| EtOH | 0.286% |

Example 6b

Demonstration of stability, 20 h of stirring at 70° C. Reprocessing of the Crude Product: Reduction of the Proportion of (+)-O,O-dibenzoyl-D-tartaric Acid (III)<0.1%

A crude product which, according to analysis, still contains 0.77% of (+)-O,O-dibenzoyl-D-tartaric acid (III) was used for reprocessing. The following procedure was adopted:

150 g of crude product (I) (containing 0.77% of (+)-O, O-dibenzoyl-D-tartaric acid (III)) were added into 600 g of water and 953.9 g of spirits and heated to 70° C. Over a period of one hour, the entire solid went into solution. The mixture was then stirred at 70° C. for 30 minutes. The pH is pH=5.0. By addition of 45.2 g of an aqueous sodium phosphate solution (15 g of sodium phosphate per 985 g of water), the pH was adjusted to pH=8.5 and the mixture was then stirred at 70° C. for 20 hours. Over a period of 30 minutes, the mixture was cooled to 53° C. and seeded with pure material (seed crystals). Stirring was then continued at 50-52° C. for 30 minutes. At 200 to 155 mbar and an internal temperature, the ethanol was distilled off virtually completely, and at the same time 1845 ml of water were metered in (the filling level was kept constant: amount distilled off=amount of water added). Heating was switched off and the suspension was stirred at 23° C. overnight. The crystals were filtered off via a frit and washed three times with 300 ml of water in each case. Wet yield: 194.3 g. The wet product was dried at 50° C. overnight (about 16 hours) under reduced pressure (<100 mbar). Yield: 143.1 g (95.4% of theory)

| Finerenone (I) | Purity: 99.86 area % (HPLC); Content: 101.3% by weight |
|---|---|
| enantiomeric excess | 97.85% e.e. |
| (+)-O,O-Dibenzoyl-D-tartaric acid | 0.00 area % (0.024% by weight) |
| Largest secondary component impurity E | 0.07% |
| Residual solvent: | |
| EtOH | 0.128% |

Example 6c

Reprocessing of the Crude Product: Reduction of the Proportion of (+)-O,O-dibenzoyl-D-tartaric Acid (III)<0.1% Backtitration of the pH to pH 7.0 with Sodium Dihydrogen Phosphate A crude product which, according to analysis, still contains 0.77% of (+)-O,O-dibenzoyl-D-tartaric acid (III) was used for reprocessing. The following procedure was adopted:

375.0 g of crude product (I) (containing 0.77% of (+)-O, O-dibenzoyl-D-tartaric acid (III)) were added into 1500 g of water and 2384.8 g of spirits and heated to 70° C. Over a period of one hour, the entire solid went into solution. The mixture was then stirred at 70° C. for 30 minutes. The pH is pH=4.9. By addition of 101.4 g of an aqueous sodium phosphate solution (15 g of sodium phosphate per 985 g of water), the pH was adjusted to pH=8.5 and the mixture was then stirred at 70° C. for 20 hours. Subsequently, the pH was adjusted to pH=7 using a sodium dihydrogen phosphate solution (50 g of sodium dihydrogen phosphate in 200 ml of water). Over a period of 30 minutes, the mixture was cooled to 53° C. and seeded with pure material (seed crystals). Stirring was then continued at 50-52° C. for 30 minutes. At 200 to 155 mbar and an internal temperature, the ethanol was distilled off virtually completely, and at the same time 4610 ml of water were metered in (the filling level was kept constant: amount distilled off=amount of water added). Finally, the mixture was cooled to 23° C. over 90 minutes.

Then the reaction mixture was stirred at 22° C. over the weekend (about 70 h). The crystals were filtered off via a frit and washed three times with 750 ml of water in each case. Wet yield: 402.3 g. The wet product was dried at 50° C. overnight (about 16 hours) under reduced pressure (<100 mbar). Yield: 336.6 g (89.76% of theory)

| Crude finerenone (I) | Purity: 99.84 area % (HPLC); Content: 99.2% by weight |
|---|---|
| enantiomeric excess | 98.02% e.e. |
| (+)-O,O-Dibenzoyl-D-tartaric acid | 0.00 area % (0.0068% by weight) |
| Largest secondary component impurity E | 0.07% |
| Residual solvents: | |
| EtOH | 0.107% |
| toluene | 0.001% |

Example 6d

Final Crystallization of the Batch from Example 6c 80.0 g of the crude product (I) prepared in Example 6c were suspended in 1600 ml of ethanol (denatured with toluene) and then heated to reflux. On heating, the product went into solution. Stirring was continued at this temperature for one hour. The solution was filtered off through a heated pressure filter (T=75° C.) and the pressure filter was then rinsed with 100 ml of ethanol (denatured with toluene). The solvent was then distilled off as gently as possible under reduced pressure (mantle temperature 45-47° C.) until an end volume of about 5-fold (with respect to the substance employed: 80 g×5~400 ml) had been achieved. Then, over one hour, the mixture was cooled to an internal temperature of 2° C. and stirred at this temperature for 1 h. The product was filtered off and rinsed once with 80 ml of ethanol (denatured with toluene). Wet yield: 83.3 g. The wet product was dried at 50° C. overnight (about 16 h) under reduced pressure (<100 mbar). Yield: 71.4 g (89.3% of theory) of a colourless crystalline powder, fine needle-like crystals.
Analytical Results:

| Finerenone (I) | Purity: 99.82 area % (HPLC); Content: 98.7% by weight |
|---|---|
| enantiomeric excess | 99.87% e.e. |
| Largest secondary component impurity E | 0.08% |
| Residual solvents: | |
| EtOH | 0.489% |
| toluene | 0.005% |

Example 7

Isolation of the finerenone enantiomer (Ia)

Example 7a

Preparation of the (−)-O,O-dibenzoyl-L-tartaric Acid Salt 187.2 g racemate (II) were initially charged at room temperature and 1662.5 g of spirits were then added. 485.5 g of water were then added. 97.5 g of (−)-O,O-dibenzoyl-L-tartaric acid (IIIa) were added using a funnel for solids, subsequently rinsing with 156.0 g of water. The suspension was heated to an internal temperature of 75° C. over one hour and then stirred at 75° C. for 3 hours. Subsequently, using a cooling ramp, the mixture was cooled to 23° C. over 5.0 hours and then stirred at this temperature overnight (about 18 hours). The suspension was filtered off through a frit and washed twice with a mixture consisting of 178 g of spirits and 75 g of water. Wet yield: 255.4 g. The wet product was then dried overnight (about 16 hours) at 50° C. under reduced pressure (<100 mbar). Yield: 188.6 g (100.73% of theory) of a colourless crystalline powder. The mother liquor and the wash solution were combined (about 3200 ml of a yellowish solution, pH=4.6) and the crude finerenone (I) was isolated therefrom (Example 7b)

| Finerenone enantiomer (Ia) | 49.3% by weight (HPLC) |
|---|---|
| enantiomeric excess | 97.35% e.e. |
| Residual solvents: | |
| EtOH | 1.847% |
| toluene | 0.00% |

In a manner analogous to that described in Examples 1b and 1c, the enantiomer of finerenone (Ia) can be prepared from this tartrate salt.

Example 7b

Isolation of Crude Finerenone (I) from the Mother Liquor

At room temperature, combined mother liquor and wash solution from Example 7a (about 3200 ml of a yellowish solution, pH=4.6) were adjusted to pH=7.6 by addition of 43.3 g of an aqueous sodium phosphate solution (100 g dissolved in 1 l of water). Under reduced pressure (85 to 65 mbar, internal temperature 38 to 20° C.), the spirits were then substantially distilled off and the mixture was reduced to an end volume of about 0.8 l. The mixture was cooled to room temperature and the precipitated suspension was stirred at 22° C. for 2 hours. The suspension was filtered off with suction and washed twice with in each case 150 ml of water. Wet yield: 159.1 g. The wet product was dried at 50° C. overnight (about 16 h) under reduced pressure (<100 mbar). Yield: 86.3 g (92.2% of theory based on the racemate (LI) employed in Example 7a).

| Finerenone (I) | Purity: 99.48 area % (HPLC); Content: 99.39% by weight |
|---|---|
| enantiomeric excess | 98.14% e.e. |
| Largest secondary component impurity E | 0.13% |
| (−)-O,O-Dibenzoyl-L-tartaric acid | 0.14% (0.05% by weight) |

In an analogous manner, as described in Example 1c, this crude product can be employed to produce finerenone (I) in pure form.

Example 8

Example 8a

Isolation of the Wrong Enantiomer (Ia) from the Mother Liquor

At room temperature, combined mother liquor and wash solution from Example 1a (about 3750 ml of a yellowish solution, pH=4.5) were adjusted to pH=7.5 by addition of 101.1 g of an aqueous sodium phosphate solution (100 g dissolved in 1 l of water). Under reduced pressure (85 to 65 mbar, internal temperature 38 to 20° C.), the spirits were then substantially distilled off and the mixture was reduced to an end volume of about 0.85 l. The mixture was cooled to room temperature and the precipitated suspension was stirred over the weekend (>48 hours) and then at 22° C. for a further 2 hours. The suspension was filtered off with suction and washed twice with in each case 200 ml of water. Wet yield: 139.1 g. The wet product was dried at 50° C. overnight (about 16 h) under reduced pressure (<100 mbar). Yield: 103.1 g (82.48% of theory based on the racemate (II) employed in Example Ia).

| Finerenone enantiomer (Ia) | Purity: 99.75 area % (HPLC); Content: 99.2% by weight |
|---|---|
| enantiomeric excess | 99.34% e.e. |
| Largest secondary component impurity E | 0.12% |
| (+)-O,O-Dibenzoyl-D-tartaric acid | 0.14% (0.05% by weight) |
| Water | 0.102% |

Example 8b

Industrial Batch for Isolation of the Finerenone Enantiomer (Ia)

A combined mother liquor and wash solution from Example 4 (tartrate preparation on an industrial scale) was worked up as follows: Amount about 1165 kg of solution
  Preparation of a sodium phosphate solution: At 20° C., 7.3 kg of sodium phosphate were dissolved in 73.1 kg of water
  In a 1600 l stirred vessel, 1165 kg of mother liquor (including wash solution) were initially charged at 20° C. and adjusted to pH 7.5 (+/−0.1) using 28 kg of the sodium phosphate solution prepared above
  The mixture was stirred for 0.25 h, and subsequently spirits were distilled off under reduced pressure (65 mbar, IT about 22° C.) to a filling level of about 310 l
  The mixture was then stirred at 20° C. for 2 h and the suspension was isolated using an inverting centrifuge, washing with 20 kg of water in each case.
  The wet product was then dried in a spherical dryer at 50° C. under reduced pressure (30 mbar; about 6 h)
  The mixture was cooled to 15° C. and the product was removed
  Analytical data of the mother liquor (incl. wash solution) employed for Batch 1

| Finerenone enantiomer (Ia) | 92.4% (HPLC) |
|---|---|
| Enantiomeric excess | 95.92 |
| Largest secondary component impurity E | 0.26% |
| (+)-O,O-Dibenzoyl-D-tartaric acid | 5.38% (HPLC) |
| Residual solvents: | |
| ethanol | 0.319% |
| toluene | 0.001% |

Analytical data of the mother liquor (incl. wash solution) employed for Batch 2

| Finerenone enantiomer (Ia) | 92.03% |
|---|---|
| enantiomeric excess | 99.03 |
| Largest secondary component impurity E | 0.15% |
| (+)-O,O-Dibenzoyl-D-tartaric acid | 5.94% |
| Residual solvents: | |
| ethanol | 0.177% |
| toluene | 0.001% |

| Batch | Input kg | Yield: kg | field: % of theory |
|---|---|---|---|
| Batch 1 | ~1165 of mother liquor (incl. wash solution) | 38.2 | 96 |
| Batch 2 | ~1165 of mother liquor (incl. wash solution) | 37.1 | 93 |

Analytical Data Batch 1

| Finerenone enantiomer (Ia) | Purity: 99.71% |
|---|---|
| enantiomeric excess | 96.56% e.e. |
| Largest secondary component impurity E | 0.106% |
| (+)-O,O-Dibenzoyl-D-tartaric acid | 0.081% |

Analytical Data Batch 2

| Finerenone enantiomer (Ia) | Purity: 99.446% |
|---|---|
| enantiomeric excess | 99.5% e.e. |
| Largest secondary component impurity E | 0.107% |
| (+)-O,O-Dibenzoyl-D-tartaric acid | 0.33% |

Example 9

Examples of further tartaric acid derivatives and further solvents

Example 9a (+)-O,O-Di-p-anisoyl-D-tartaric Acid 100 mg of racemate and 111 mg of (+)-O,O-di-p-anisoyl-D-tartaric acid were dissolved in 5 ml of dichloromethane and allowed to stand. After some time, the diastereomeric salt precipitated out. The salt was filtered off and the enantiomeric excess was measured. The measurement showed an enantiomeric excess of 68% e.e. for (Ia)

Example 9b (−)-O,O'-Di-p-toluyl-L-tartaric Acid 100 mg of racemate and 0.55 eq. of (−)-O,O-di-p-toluyl-L-tartaric acid were dissolved in 4 ml of solvent and allowed to stand. After some time, the diastereomeric salt precipitated out. The salt was filtered off and the enantiomeric excess was measured. The measurement showed an enantiomeric excess of y % e.e. for (Ia). The results are summarized in Table 7 below.

TABLE 7

| 4 ml of solvent/solvent mixture | Enantiomeric excess e.e. % (Ia) |
|---|---|
| n-propanol/water 80:20 | 85.35 |
| n-pentanol/water 90:10 | 89.10 |
| methanol/water 80:20 | 84.47 |
| methanol | 93.18 |
| isopropanol/water 80:20 | 81.20 |
| isobutanol/water 90:10 | 79.25 |
| ethylene glycol/water 80:20 | 93.68 |
| ethylene glycol | 68.50 |
| ethanol/water 80:20 | 85.87 |
| ethanol | 85.96 |
| 2-butanol/water 80:20 | 83.92 |
| 1-butanol/water 90:10 | 88.93 |

Example 9c

(+)-O,O-Dibenzoyl-D-tartaric Acid 100 mg of racemate and 0.55 eq. of (+)-O,O-dibenzoyl-D-tartaric acid were dissolved in 4 ml of solvent and allowed to stand. After some time, the diastereomeric salt precipitated out. The salt was filtered off and the enantiomeric excess was measured. The measurement showed an enantiomeric excess of y % e.e. for (I). The results are summarized in Table 8 below.

TABLE 8

| 4 ml of solvent/solvent mixture | Enantiomeric excess e.e. % (I) |
|---|---|
| n-propanol/water 80:20 | 94.01 |
| n-pentanol/water 90:10 | 94.59 |
| methanol/water 80:20 | 89.09 |
| methanol | 91.21 |
| isopropanol/water 80:20 | 90.92 |
| isobutanol/water 90:10 | 85.42 |
| ethyl glycol | 92.08 |
| ethanol/water 80:20 | 94.64 |
| ethanol | 93.64 |
| cyclohexanol/water 90:10 | 84.33 |
| benzyl alcohol/water 90:10 | 88.83 |
| 2-butanol/water 80:20 | 92.49 |
| 1-pentanol | 80.99 |
| 1-butanol/water 90:10 | 94.02 |

The invention claimed is:

1. A process for resolving a racemic mixture of formula (II)

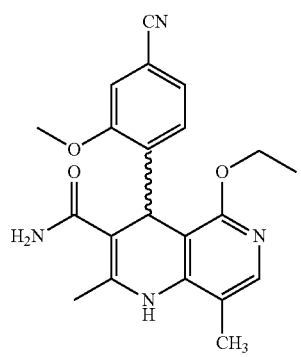
(R,S-II)

into (Ia) and/or (I)

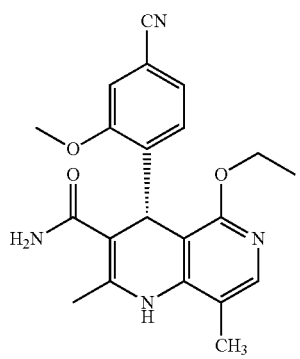
(Ia)

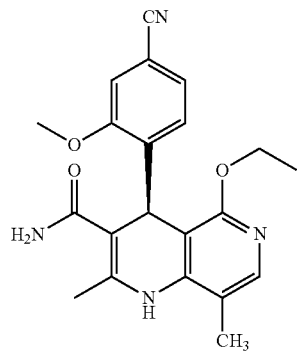
(I)

comprising reacting the racemic mixture of formula (II) with a chiral substituted tartaric ester of formulae (IIIa) or (IIIb)

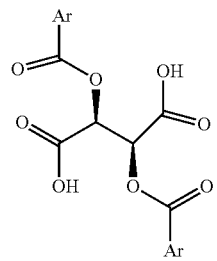
(IIIa)

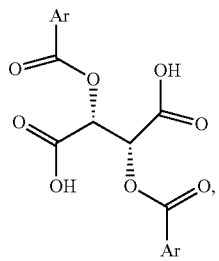
(IIIb)

wherein Ar represents

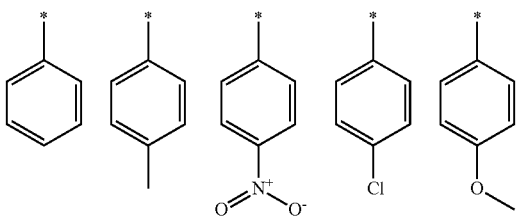

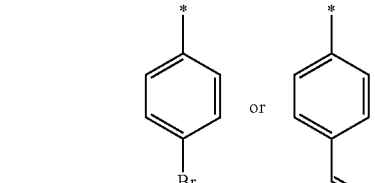

wherein * represents the point of attachment.

2. A process for preparing (4S)-4-(4-cyano-2-methoxyphenyl)-5-ethoxy-2,8-dimethyl-1,4-dihydro-1,6-naphthyridine-3-carboxamide of the formula (I)

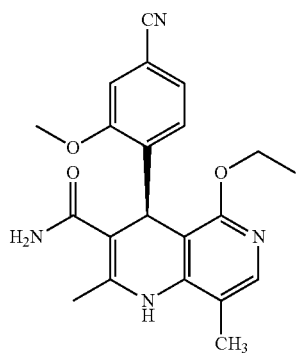
(I)

comprising resolving the racemates of the compound of formula (II)

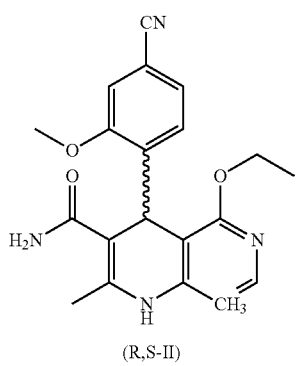 [SMILES: CCOc1nccc2c1C(c1ccc(C#N)cc1OC)C(C(N)=O)=C(C)N2]
(R,S-II)

by reacting the compound of formula (II) with a chiral substituted tartaric ester of formula (IIIa)

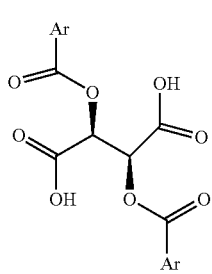
(IIIa)

wherein Ar represents

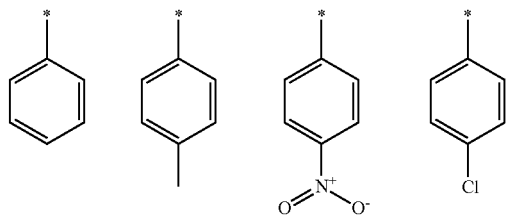

-continued

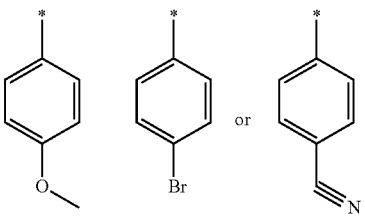

wherein * represents the point of attachment.

3. The process of claim 1, wherein the racemic mixture of formula (II) is reacted with the chiral substituted tartaric ester of formulae (IIIa) or (IIIb) in an ethanol/water mixture.

4. The process of claim 2, wherein the racemate resolution is carried out in an ethanol/water mixture.

5. The process of claim 1, wherein the racemic mixture of formula (II) is reacted with the chiral substituted tartaric ester of formulae (IIIa) or (IIIb) at a temperature in the range from 60 to 80° C.

6. The process of claim 2, wherein the racemate resolution is carried out at a temperature in the range from 60 to 80° C.

7. The process of claim 1, wherein Ar represents

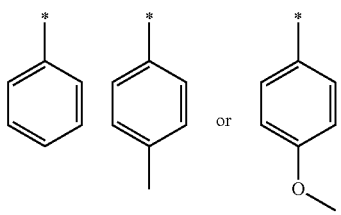

wherein * represents the point of attachment.

8. The process of claim 2, wherein Ar represents

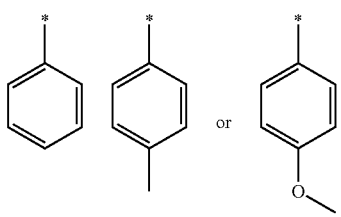

wherein * represents the point of attachment.

9. The process of claim 1, wherein Ar represents phenyl.

10. The process of claim 2, wherein Ar represents phenyl.

11. The process of claim 1, wherein the chiral substituted tartaric ester of formula (IIIa) is dibenzoyltartaric acid of the formula (III)

(III)

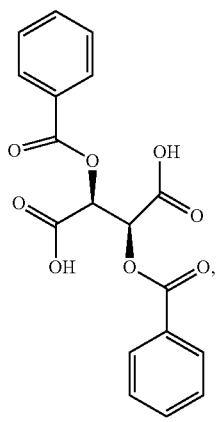

12. The process of claim 2, wherein the chiral substituted tartaric ester of formula (IIIa) is dibenzoyltartaric acid of the formula (III)

(III)

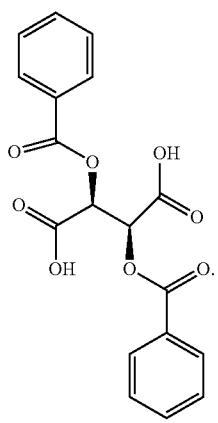

13. The process of claim 1, wherein reacting the racemic mixture of formula (II) with the chiral substituted tartaric ester of formulae (IIIa) or (IIIb) yields at least one of the diastereomeric salts of the formulae (IVa), (IVb), (IVc) and/or (IVd)

(IVa)

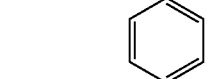

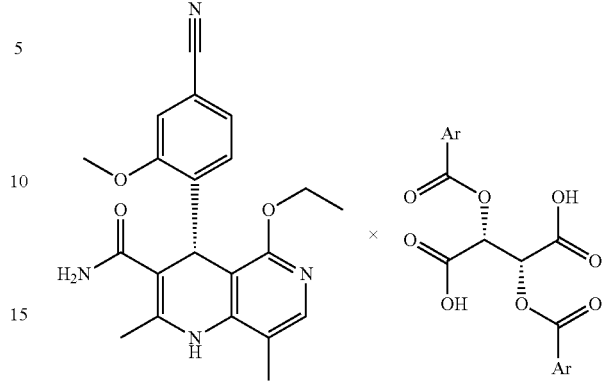

(IVb)

(IVc)

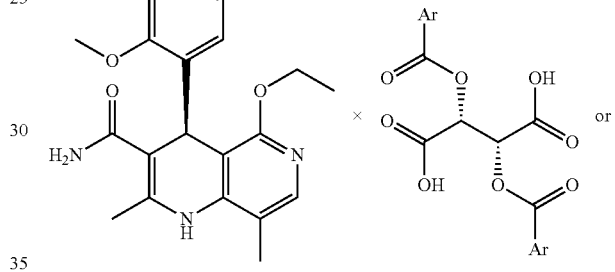

or (IVd)

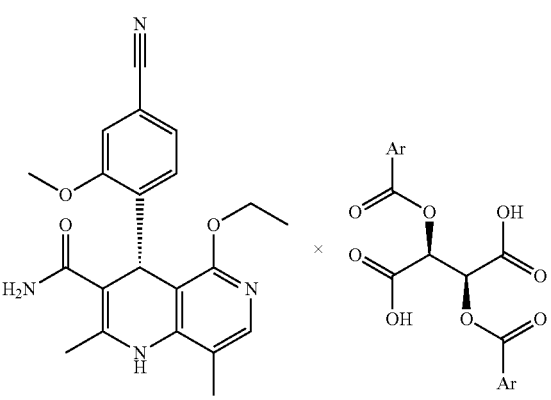

wherein Ar represents

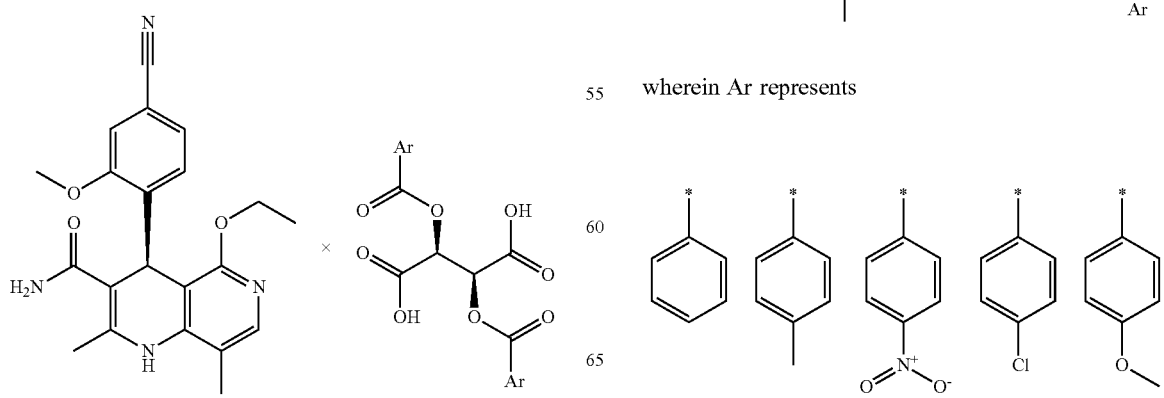

-continued

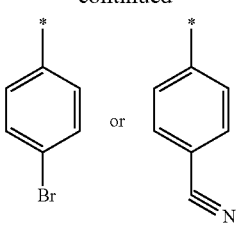

wherein * represents the point of attachment.

14. The process of claim 2, wherein reacting the racemic mixture of formula (II) with the chiral substituted tartaric ester of formulae (IIIa) or (IIIb) yields at least one of the diastereomeric salts of the formulae (IVa) and/or (IVc)

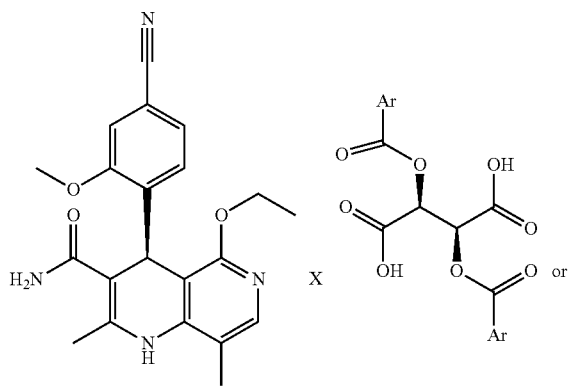

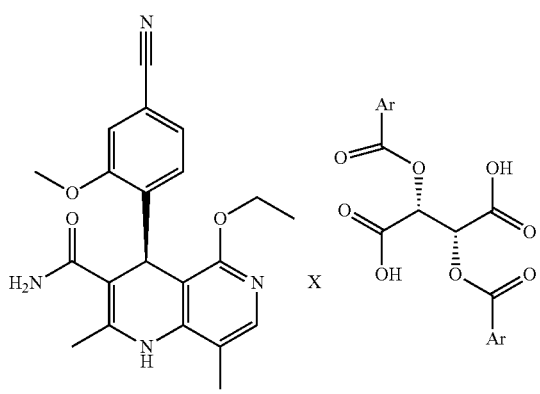

wherein Ar represents

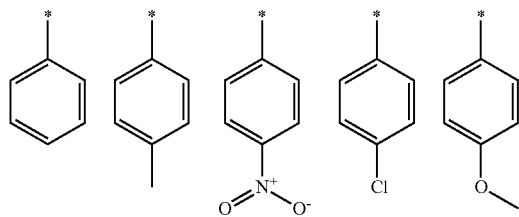

-continued

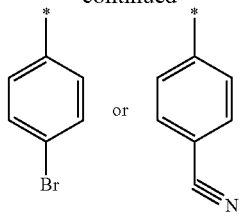

wherein * represents the point of attachment.

15. The process of claim 13, wherein the diastereomeric salt of the formulae (IVa), (IVb), (IVc) and/or (IVd) is precipitated.

16. The process of claim 14, wherein the diastereomeric salt of the formulae (IVa) and/or (IVc) is precipitated.

17. The process of claim 13, wherein the formation of diastereomeric salts takes place in solvent mixtures consisting of water and water-miscible organic solvents.

18. The process of claim 14, wherein the formation of diastereomeric salts takes place in solvent mixtures consisting of water and water-miscible organic solvents.

19. The process of claim 15, further comprising isolating the precipitated diastereomeric salt (IVa), (IVb), (IVc) and/or (IVd).

20. The process of claim 16, further comprising isolating the precipitated diastereomeric salt (IVa) and/or (IVc).

21. The process of claim 13, wherein the racemic mixture of formula (II) is reacted with the chiral substituted tartaric ester of formulae (IIIa) or (IIIb) in the presence of a solvent, and further wherein the diastereomeric salt is treated with a base and the solvent is removed.

22. The process of claim 14, wherein the racemic mixture of formula (II) is reacted with the chiral substituted tartaric ester of formulae (IIIa) or (IIIb) in the presence of a solvent, and further wherein the diastereomeric salt is treated with a base and the solvent is removed.

23. The process of claim 21, wherein the base is potassium hydroxide, potassium phosphate or sodium phosphate.

24. The process of claim 22, wherein the base is potassium hydroxide, potassium phosphate or sodium phosphate.

25. The process of claim 17, wherein the formation of diastereomeric salts takes place in solvent mixtures consisting of water and water-miscible organic solvents selected from ethanol, isopropanol, 1,2-ethanediol, methoxyethanol, methanol, acetone, spirit and mixtures thereof.

26. The process of claim 18, wherein the formation of diastereomeric salts takes place in solvent mixtures consisting of water and water-miscible organic solvents selected from ethanol, isopropanol, 1,2-ethanediol, methoxyethanol, methanol, acetone, spirits and mixtures thereof.

27. The process of claim 1, wherein the racemic mixture of formula (II)

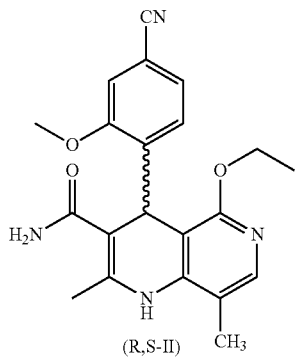 [SMILES: CCOc1ncc(C)c2c1C(c1ccc(C#N)cc1OC)C(C(N)=O)=C(C)N2]

(R,S-II)

is reacted with dibenzoyltartaric acid of the formula (III)

(III)

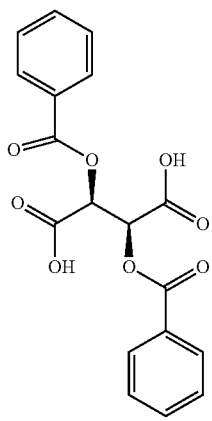

in a spirits/water mixture to give the diastereomeric salt (VI)

(VI)

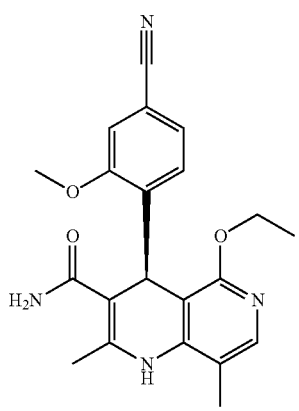

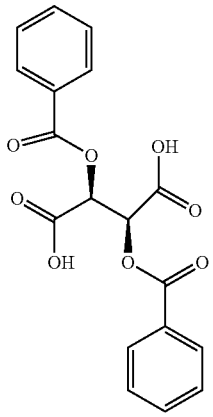

and subsequently the compound of formula (I)

(I)

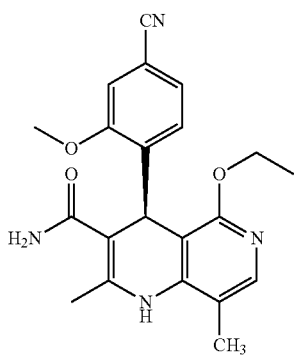

is released by the addition of sodium phosphate, the addition occurring in a spirits/water mixture.

28. The process of claim 2, wherein the racemic mixture of formula (II)

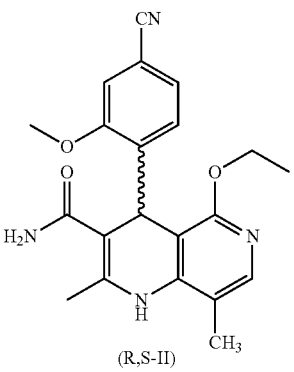 [SMILES: CCOc1ncc(C)c2c1C(c1ccc(C#N)cc1OC)C(C(N)=O)=C(C)N2]

(R,S-II)

is reacted with the chiral substituted tartaric ester of formula (IIIa) that is dibenzoyltartaric acid of the formula (III)

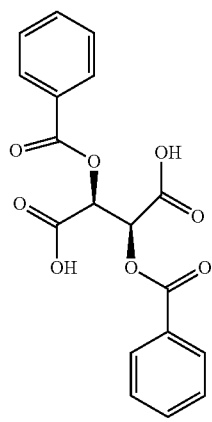
(III)
in a spirits/water mixture to give the diastereomeric salt (VI)
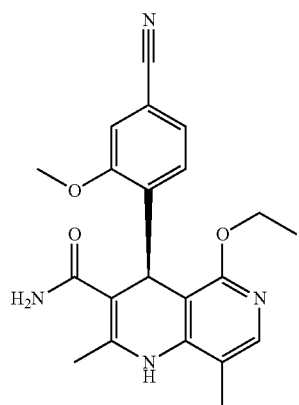
(VI)
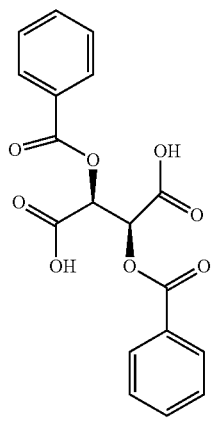
and subsequently the compound of formula (I)
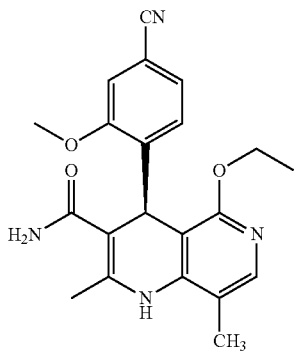
(I)
is released by the addition of sodium phosphate, the addition occurring in a spirits/water mixture.
29. A diastereomeric salt of the formula
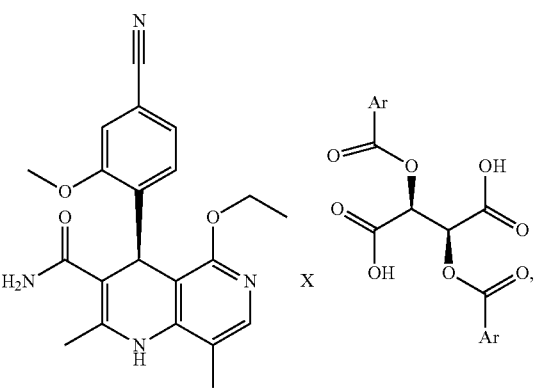
(IVa)
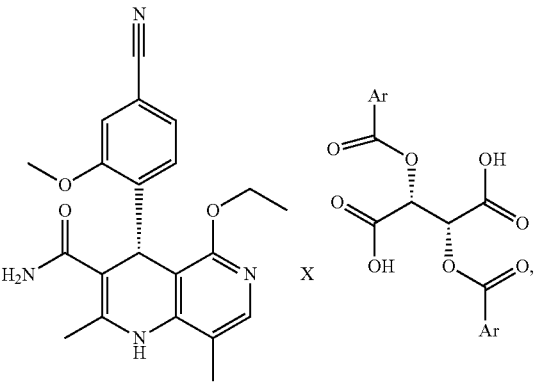
(IVb)

-continued (IVc)

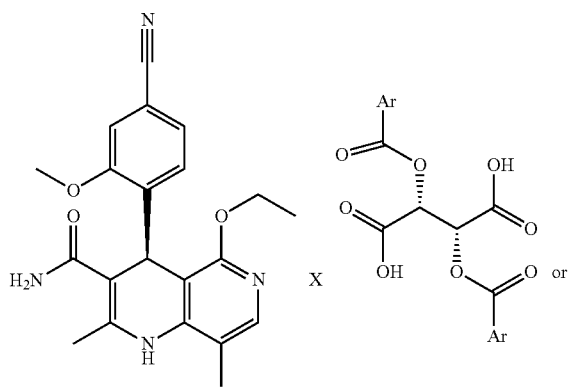

X

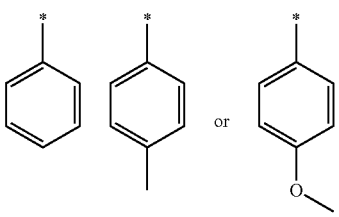

or (IVd)

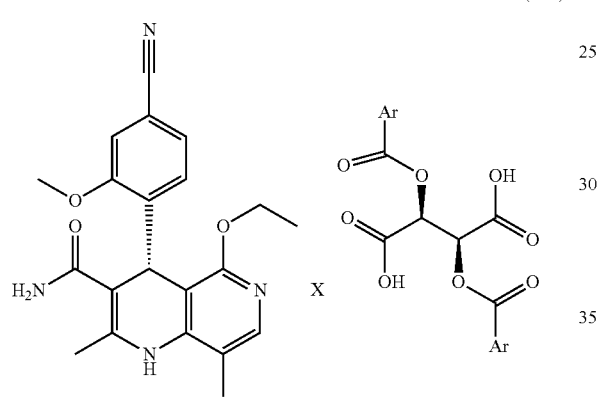

X wherein Ar represents

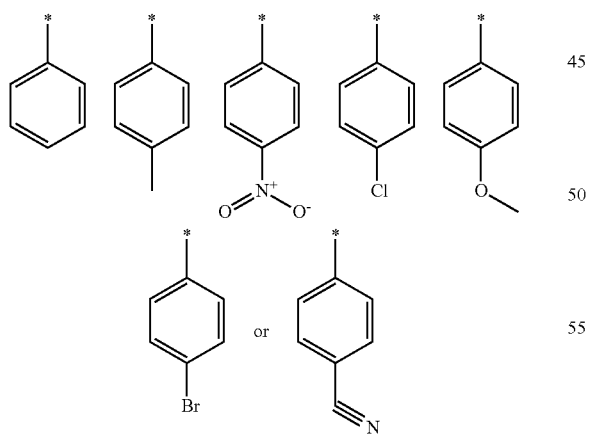

wherein * represents the point of attachment.

30. The diastereomeric salt of claim 29, wherein Ar represents

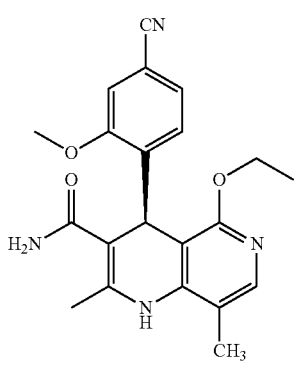

or wherein * represents the point of attachment.

31. The diastereomeric salt of claim 29, wherein Ar represents phenyl.

32. A composition comprising a compound of formula (I)

(I)

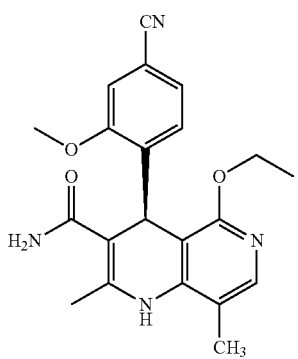

and dibenzoyltartaric acid, wherein the dibenzoyltartaric acid is present at >0.15% by weight of the compound of formula (I).

33. The composition of claim 32 in crystalline form.

34. A composition comprising a compound of formula (I)

(I)

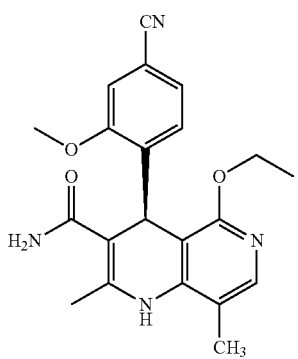

and dibenzoyltartaric acid, wherein the dibenzoyltartaric acid is present at >0.15% by weight of the compound of formula (I), wherein the compound of formula (I) is prepared by the process of claim 2.

* * * * *

UNITED STATES PATENT AND TRADEMARK OFFICE
CERTIFICATE OF CORRECTION

| | |
|---|---|
| PATENT NO. | : 12,054,481 B2 |
| APPLICATION NO. | : 17/050303 |
| DATED | : August 6, 2024 |
| INVENTOR(S) | : Platzek et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 919 days.

Signed and Sealed this
Fifth Day of November, 2024

Katherine Kelly Vidal
*Director of the United States Patent and Trademark Office*